United States Patent [19]
Weiser

[11] Patent Number: 5,871,951
[45] Date of Patent: Feb. 16, 1999

[54] **COMPOSITIONS AND METHODS FOR TREATMENT OF INFECTION CAUSED BY *HAEMOPHILUS INFLUENZAE* AND *STREPTOCOCCUS PNEUMONIAE***

[75] Inventor: Jeffrey N. Weiser, Merion, Pa.

[73] Assignee: The Children's Hospital of Philadelphia, Philadelphia, Pa.

[21] Appl. No.: 935,396

[22] Filed: Sep. 23, 1997

Related U.S. Application Data

[60] Provisional application No. 60/026,940 Sep. 23, 1996.
[51] Int. Cl.$^6$ .............................. C12Q 1/02; C12Q 1/50; C12Q 1/00
[52] U.S. Cl. ................................ 435/29; 435/17; 435/4; 435/253.4; 435/885; 435/851; 435/32
[58] Field of Search ................................ 435/29, 17, 4, 435/253.4, 885, 851, 32

[56] References Cited

PUBLICATIONS

Altschul et al., 1990, J. Mol. Biol. 215:403–410.
Beiss, 1964, J. Chromatography 13:104–110.
Berry et al. 1995, Infect. Immun. 63:1969–1974.
Fischer et al., 1993, Eur. J. Biochem. 215:851–857.
Fischer et al., 1983, Eur. J. Biochem. 133:523–530.
Fleischmann et al., 1995, Science 269:497–512.
Flugge et al., 1991, Nature 353:364–367.
Glaser et al., 1993, Mol. Microbiol. 10:371–384.
Guidolin et al., 1994, Infect. Immun. 62:5384–5396.
Gulig, et al., 1987, Infect. Immun. 55:513–520.
Harlow et al., 1988, In: Antibodies, A Laboratory Manual, Cold Spring Harbor, NY (too voluminous to submit).
Herriot et al., 1970, J. Bacteriol., 101:517–524.
High et al., 1993, Mol. Microbiol. 9:1275–1282.
Hitchcock et al., 1983, J. Bacteriol. 154:269–277.
Hoiseth et al., 1995, Infect. Immun. 49:389–395.
Inzana, 1983, J. Infect. Dis. 148:492–499.
Johnson et al., 1976, Can. J. Microbiol. 22:29–34.
Kimura et al., 1987, Infect. Immun. 55:1979–1986.
Kimura et al., 1986, Infect. Immun. 51:69–79.
Klugman, 1990, Clin. Microbiol. Rev. 3:171–196.
Ladefoged et al., 1994, J. Bacteriol. 176:5835–5842.
Lamark et al., 1991, Mol. Microbiol. 5:1049–1064.
Leon et al., 1971, Biochemistry 10:1424–1429.
Maskell et al., 1991, Mol. Microbiol. 5:1013–1022.
Michalka, 1969, J. Mol. Biol. 45:407–421.
Mosser et al., 1970, J. Biol. Chem. 245:287–298.
Moxon et al., 1991, Rev. Inf. Dis. 13(suppl.):s518.
Phillips et al., 1993, Biochemistry 32:2003–201.
Povdin et al., 1988, J. Gen. Microbiol. 134:1603–1609.
Raetz, 1996, In: *Escherichia coli and Salmonella*, pp. 1035–1063, Neidhardt, Eds., ASM Press, Washington, D.C.
Repo et al., 1987, Am. Soc. for Microbiology, pp. 507–512.
Schwarz et al., 1994, J. Biol. Chem. 269:29481–29489.
Schweda et al., 1993, Carbohydrate Research 246:319–330.
Thomas et al., 1978, J. Gen. Microbiology, 109:313–317.
Towbin et al., 1979, Proc. Natl. Acad. Sci. USA 76:4350–4354.
Tuomanen et al., 1995, New Engl. J. Med. 332:1280–1284.

(List continued on next page.)

*Primary Examiner*—Louise N. Leary
*Attorney, Agent, or Firm*—Panitch Schwarze Jacobs & Nadel, P.C.

[57] ABSTRACT

The invention relates to a method of identifying a compound capable of disrupting the addition of choline onto a bacterial cell surface component comprising incubating a sample of bacteria in a solution containing choline in the presence or absence of a test compound, and assessing the effect of the test compound on the addition of choline onto the bacterial cell surface component, wherein a lower level of choline on the cell surface component in the presence of the test compound, compared with the level of choline on the cell surface component in the absence of the test compound, is an indication that the test compound inhibits the addition of choline onto the cell surface component.

15 Claims, 11 Drawing Sheets

PUBLICATIONS

Uchida et al., 1992, J. Biol. Chem. 267:10156–10162.
Weiser et al., 1989, Infect. Immun. 57:3045–3052.
Weiser et al., 1990, J. Bacteriology 172:3304–3309.
Weiser et al., 1990, Infect. Immun. 58:3455–3457.
Weiser, 1993, J. Infect. Dis. 168:672–680.
Weiser et al., 1994, Infect. Immun. 62:2582–2589.
Weiser et al., 1989, *Cell* 59:657–665.
Whiting et al., 1996, FEMS Microbiology Lett. 138:141–145.
Zamze et al., 1987, Biochem. J. 245:583–587.
Zamze et al., 1987, J. Gen. Microbiol. 133:1443–1451.
Zwahlen et al., 1986, Microbial. Pathogenesis 1:465–473.

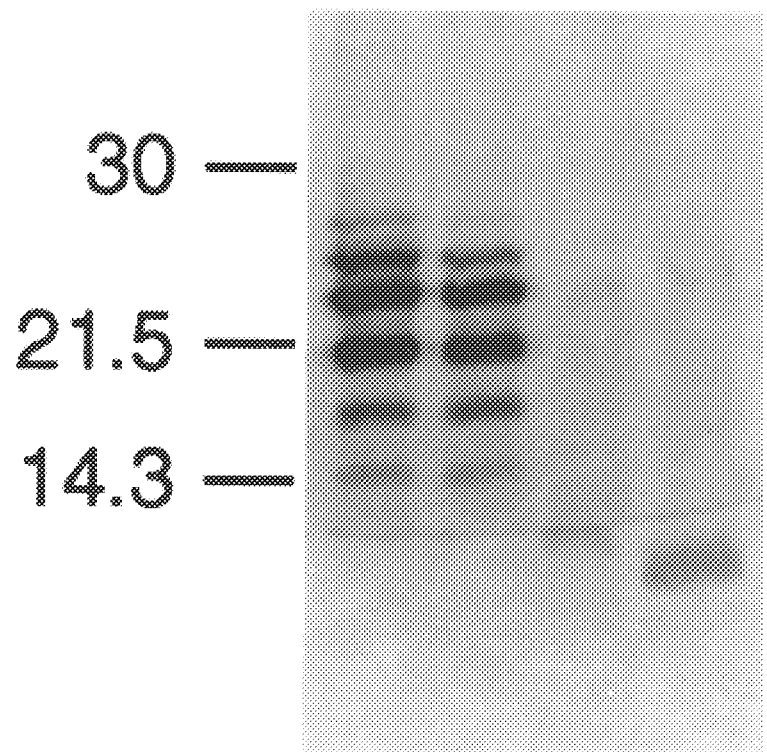

QUATERNARY AMINE

```
LicA (H.influenzae)         222  CHNDLVPENMLL------QDDRLFFFIDWEYSGLNDPLFDIATIIEEA        262
                                 ||||   ||         ||||| ||||||||||||||||||||||
Choline kinase (S.cerevisiae) 327 CHNDAQYGNLLFTA*QEQSQDSKLVVIDFEYAGANPAAYDLANHLSEW      414

LicA (H. influenzae)        222  CHNDLVPENMLL------QDDRLFFFIDWEYSGLNDPLFDIATIIEEA        262
                                 ||||   ||         |||||   |||
Choline kinase (C. elegans) 158  CHNDLTSSNILQ------LNSTGELVFIDWENASYNWRGYDLAMHLSEA       200

LicA (H.influenzae)         222  CHNDLVPENMLL------QDDRLFFFIDWEYSGLNDPLFDIATIIEEA        262
                                 ||||  |           |    |||||||
Choline kinase (R.norvegicus) 394 CHNDCQEGNILLEGQENSEKQKLMLIDFEYSSYNYRGFDIGNHFCEW        352

LicA (H.influenzae)         205  CHNDLVPENMLL------QDDRLFFFIDWEYSGLNDPLFDIATIIEEA        245
                                 ||||  |                   ||||| |
LicA (M.hominus)            142  VHNDLWLFNMIK------VNDKIYFTDWEYATMGDVHFDLAYFIESS        182
```

Fig. 6

*S. pneumoniae* licA gene (partial)

```
AAGCTTATCA ATCGACAAGA TGAAAAGTAC AATCTTGAAC TACTAAAGGA
TTTAGGCTTA GATGTAAAAA ATTATCTTTT TGATATTGAA GCTGGCATCA
AAGTAAATGA GTATATCGAA TCTGCGATTA CGCTTGATTC AACGTCAATC
AAGACCAAGT TCGACAAAAT TGCTCCAATA TTACAAACTA TTCATACATC
TGCTAAGGAA TTAAGAGGAG AATTTGCTCC TTTTGAAGAA ATCAAAAAAT
ACGAATCCTT GATTGAAGAA CAAATTCCTT ATGCCAACTA TGAATCTGTT
AGAAATGCAG TCTTCTCCTT AGAGAAAAGA CTGGCTGACT TAGGTGTTGA
CAGAAAATCT TGTCATATCG ATTTGGTGCC TGAAAACTTT ATCGAATCAC
CTCAAGGACG ACTTTATTTG ATTGACTGGG AATATTCATC AATGAATGAT
CCAATGTGGG ATTTGGCTGC CCTCTTTTTA GAGTCTGAAT TCACTTCCCA
AGAGGAAGAA ACTTTCTTAT CTCACTATGA GAGTGACCAA ACACCGGTTT
CTCATGAAAA GATTGCTATT TATAAAATTT TACAAGATAC TATTTGGAGT
CTATGGACTG TCTATAAAGA AGAACACGGT GAAAACTTCG GCGACTAC
```

*S. pneumoniae* licA protein (partial)

```
KLINRQDEKY NLELLKDLGL DVKNYLFDIE AGIKVNEYIE SAITLDSTSI
KTKFDKIAPI LQTIHTSAKE LRGEFAPFEE IKKYESLIEE QIPYANYESV
RNAVFSLEKR LADLGVDRKS CHIDLVPENF IESPQGRLYL IDWEYSSMND
PMWDLAALFL ESEFTSQEEE TFLSHYESDQ TPVSHEKIAI YKILQDTIWS
LWTVYKEEHG ENFGDY
```

```
Sp       CHIDLVPENFIESPQGRLYLIDWEYSSMNDPMWDLAALFLESEFTSQEETFLSHY
         ||.||—||.:..:.|||:..:.||||—|—||:..|:..:|:..:..|—|..:..|
Hi  150  CHNDLVPENMLLQDD-RLFFIDWEYSGLNDPLFDIATIIEEAHLSKEAADFLLETY  204

Sp       ESDQTPVSHEKIAIYKILQDTIWSLWTVYKEEXGENFGDY
         ..:..|:..:.—|:..:|—||||..:.||.|||||||
Hi  212  HRTEFQIAHKRLKIHRFCQNVLWFLWTKVKEEHGENFGDY  251

Sp       CHIDLVPENFIESPQGRLYLIDWEYSSMNDPMWDLAALFLE
         ||.||—||.:..:.|||..:..:.|||:..:.|||—|..|
Mp  164  CHHDSTFDNLVYTPKKQVVLIDFEWSCVDNPYYEIANIIRE  204
```

Sequence Comparison Between *H. influenzae* and
*S. pneumoniae* choline kinase

>pir||B64128 lic-1 operon protein (licA) homolog - Haemophilus influenzae
 (strain Rd KW20) >gi|1574379 (U32829) lic-1 operon protein (licA)
 [Haemophilus influenzae]
 Length = 267
Score = 127 (57.7 bits), Expect = 8.2e-45, Sum P(5) = 8.2e-45
Identities = 19/41 (46%), Positives = 29/41 (70%)
Query:  176 YESDQTPVSHEKIAIYKILQDTIWSLWTVYKEEHGENFGDY 216
            Y  + ++H+++ I++  Q+ +W LWT  KEEHGENFGDY
Sbjct:  211 YHKTEFQIAHKRLKIHRFCQNVLWFLWTKVKEEHGENFGDY 251
Score = 85 (38.6 bits), Expect = 8.2e-45, Sum P(5) = 8.2e-45
Identities = 13/20 (65%), Positives = 18/20 (90%)
Query:  137 RLYLIDWEYSSMNDPMWDLA 156
            RL+ IDWEYS +NDP++D+A
Sbjct:  165 RLFFIDWEYSGLNDPLFDIA 184
Score = 78 (35.4 bits), Expect = 8.2e-45, Sum P(5) = 8.2e-45
Identities = 16/49 (32%), Positives = 29/49 (59%)
Query:    2 LINRQDEKYNLELLKDLGLDVKNYLFDIEAGIKVNEYIESAITLDSTSI 50
            LINR+ E +N    GL+V+  + D ++G+K+ Y+E++ TL   +
Sbjct:   27 LINREYEAFNNAQAYRAGLNVETPVLDAKSGVKLTRYLENSNTLSQIQL 75
Score = 56 (25.4 bits), Expect = 8.2e-45, Sum P(5) = 8.2e-45
Identities = 12/39 (30%), Positives = 21/39 (53%)
Query:   61 LQTIHTSAKELRGEFAPFEEIKKYESLIEEQIPYANYES 99
            L +H S   R F+ F+E ++Y SL+E +   +S
Sbjct:   88 LYRLHNSEFVFRNVFSVFDEFRQYFSLLENKSAFYQADS 126
Score = 49 (22.3 bits), Expect = 8.2e-45, Sum P(5) = 8.2e-45
Identities = 8/13 (61%), Positives = 10/13 (76%)
Query:  119 KSCHIDLVPENFI 131
            + CH DLVPEN +
Sbjct:  148 RPCHNDLVPENML 160
Score = 34 (15.4 bits), Expect = 1.5e-10, Sum P(4) = 1.5e-10
Identities = 6/19 (31%), Positives = 11/19 (57%)
Query:  191 YKILQDTIWSLWTVYKEEH 209
            Y L D ++ + T+ +E H
Sbjct:  173 YSGLNDPLFDIATIIEEAH 191

FIGURE 11

SEQUENCE LISTING ( 1 ) GENERAL INFORMATION:

( i i i ) NUMBER OF SEQUENCES: 19

( 2 ) INFORMATION FOR SEQ ID NO:1:

( i ) SEQUENCE CHARACTERISTICS:
  ( A ) LENGTH: 41 amino acids
  ( B ) TYPE: amino acid
  ( C ) STRANDEDNESS: single
  ( D ) TOPOLOGY: linear ( i i ) MOLECULE TYPE: protein ( x i ) SEQUENCE DESCRIPTION: SEQ ID NO:1:

| Cys | His | Asn | Asp | Leu | Val | Pro | Glu | Asn | Met | Leu | Leu | Gln | Asp | Asp | Arg |
| 1 | | | | 5 | | | | | 10 | | | | | 15 | |

| Leu | Phe | Phe | Ile | Asp | Trp | Glu | Tyr | Ser | Gly | Leu | Asn | Asp | Pro | Leu | Phe |
| | | | 20 | | | | 25 | | | | | 30 | | | |

| Asp | Ile | Ala | Thr | Ile | Ile | Glu | Glu | Ala |
| | | 35 | | | | 40 | | |

( 2 ) INFORMATION FOR SEQ ID NO:2:

( i ) SEQUENCE CHARACTERISTICS:
    ( A ) LENGTH: 47 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:2:

| Cys | His | Asn | Asp | Ala | Gln | Tyr | Gly | Asn | Leu | Leu | Phe | Thr | Ala | Gln | Glu |
| 1 | | | | 5 | | | | | 10 | | | | | 15 | |

| Gln | Ser | Gln | Asp | Ser | Lys | Leu | Val | Val | Ile | Asp | Phe | Glu | Tyr | Ala | Gly |
| | | | 20 | | | | | 25 | | | | | 30 | | |

| Ala | Asn | Pro | Ala | Ala | Tyr | Asp | Leu | Ala | Asn | His | Leu | Ser | Glu | Trp |
| | | | 35 | | | | 40 | | | | | 45 | | |

( 2 ) INFORMATION FOR SEQ ID NO:3:

( i ) SEQUENCE CHARACTERISTICS:
    ( A ) LENGTH: 41 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:3:

| Cys | His | Asn | Asp | Leu | Val | Pro | Glu | Asn | Met | Leu | Leu | Gln | Asp | Asp | Arg |
| 1 | | | | 5 | | | | | 10 | | | | | 15 | |

| Leu | Phe | Phe | Ile | Asp | Trp | Glu | Tyr | Ser | Gly | Leu | Asn | Asp | Pro | Leu | Phe |
| | | | 20 | | | | 25 | | | | | 30 | | | |

| Asp | Ile | Ala | Thr | Ile | Ile | Glu | Glu | Ala |
| | | 35 | | | | 40 | | |

( 2 ) INFORMATION FOR SEQ ID NO:4:

( i ) SEQUENCE CHARACTERISTICS:
    ( A ) LENGTH: 43 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:4:

| Cys | His | Asn | Asp | Leu | Thr | Ser | Ser | Asn | Ile | Leu | Gln | Leu | Asn | Ser | Thr |
| 1 | | | | 5 | | | | | 10 | | | | | 15 | |

| Gly | Glu | Leu | Val | Phe | Ile | Asp | Trp | Glu | Asn | Ala | Ser | Tyr | Asn | Trp | Arg |

|         |         |         |         |         |         |         |         |         | 20      |         |         |         |         | 25      |         |         |         |         | 30      |
|---------|---------|---------|---------|---------|---------|---------|---------|---------|---------|---------|---------|---------|---------|---------|---------|---------|---------|---------|---------|

Gly Tyr Asp Leu Ala Met His Leu Ser Glu Ala
              35                    40

( 2 ) INFORMATION FOR SEQ ID NO:5:

( i ) SEQUENCE CHARACTERISTICS:
        ( A ) LENGTH: 41 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:5:

Cys His Asn Asp Leu Val Pro Glu Asn Met Leu Leu Gln Asp Asp Arg
1               5                   10                  15

Leu Phe Phe Ile Asp Trp Glu Tyr Ser Gly Leu Asn Asp Pro Leu Phe
              20                  25                  30

Asp Ile Ala Thr Ile Ile Glu Glu Ala
              35              40

( 2 ) INFORMATION FOR SEQ ID NO:6:

( i ) SEQUENCE CHARACTERISTICS:
        ( A ) LENGTH: 48 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:6:

Cys His Asn Asp Cys Gln Glu Gly Asn Ile Leu Leu Leu Glu Gly Gln
1               5                   10                  15

Glu Asn Ser Glu Lys Gln Lys Leu Met Leu Ile Asp Phe Glu Tyr Ser
              20                  25                  30

Ser Tyr Asn Tyr Arg Gly Phe Asp Ile Gly Asn His Phe Cys Glu Trp
              35                  40                  45

( 2 ) INFORMATION FOR SEQ ID NO:7:

( i ) SEQUENCE CHARACTERISTICS:
        ( A ) LENGTH: 41 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:7:

Cys His Asn Asp Leu Val Pro Glu Asn Met Leu Leu Gln Asp Asp Arg
1               5                   10                  15

Leu Phe Phe Ile Asp Trp Glu Tyr Ser Gly Leu Asn Asp Pro Leu Phe
              20                  25                  30

Asp Ile Ala Thr Ile Ile Glu Glu Ala
              35              40

( 2 ) INFORMATION FOR SEQ ID NO:8:

( i ) SEQUENCE CHARACTERISTICS:
        ( A ) LENGTH: 41 amino acids
        ( B ) TYPE: amino acid
        ( C ) STRANDEDNESS: single
        ( D ) TOPOLOGY: linear (i i) MOLECULE TYPE: protein (x i) SEQUENCE DESCRIPTION: SEQ ID NO:8:

| Val | His | Asn | Asp | Leu | Trp | Leu | Phe | Asn | Met | Ile | Lys | Val | Asn | Asp | Lys |
|---|---|---|---|---|---|---|---|---|---|---|---|---|---|---|---|
| 1 | | | | 5 | | | | | 10 | | | | | 15 | |

| Ile | Tyr | Phe | Thr | Asp | Trp | Glu | Tyr | Ala | Thr | Met | Gly | Asp | Val | His | Phe |
|---|---|---|---|---|---|---|---|---|---|---|---|---|---|---|---|
| | | | 20 | | | | 25 | | | | | 30 | | | |

| Asp | Leu | Ala | Tyr | Phe | Ile | Glu | Ser | Ser |
|---|---|---|---|---|---|---|---|---|
| | | 35 | | | | 40 | | |

(2) INFORMATION FOR SEQ ID NO:9:

(i) SEQUENCE CHARACTERISTICS:
(A) LENGTH: 648 base pairs
(B) TYPE: nucleic acid
(C) STRANDEDNESS: single
(D) TOPOLOGY: linear (i i) MOLECULE TYPE: DNA (genomic)

(x i) SEQUENCE DESCRIPTION: SEQ ID NO:9:

```
AAGCTTATCA ATCGACAAGA TGAAAAGTAC AATCTTGAAC TACTAAAGGA TTTAGGCTTA      60
GATGTAAAAA ATTATCTTTT TGATATTGAA GCTGGCATCA AAGTAAATGA GTATATCGAA     120
TCTGCGATTA CGCTTGATTC AACGTCAATC AAGACCAAGT TCGACAAAAT TGCTCCAATA     180
TTACAAACTA TTCATACATC TGCTAAGGAA TTAAGAGGAG AATTTGCTCC TTTTGAAGAA     240
ATCAAAAAAT ACGAATCCTT GATTGAAGAA CAAATTCCTT ATGCCAACTA TGAATCTGTT     300
AGAAATGCAG TCTTCTCCTT AGAGAAAAGA CTGGCTGACT AGGTGTTGA CAGAAAATCT      360
TGTCATATCG ATTTGGTGCC TGAAAACTTT ATCGAATCAC CTCAAGGACG ACTTTATTTG     420
ATTGACTGGG AATATTCATC AATGAATGAT CCAATGTGGG ATTTGGCTGC CCTCTTTTTA     480
GAGTCTGAAT TCACTTCCCA AGAGGAAGAA ACTTTCTTAT CTCACTATGA GAGTGACCAA     540
ACACCGGTTT CTCATGAAAA GATTGCTATT TATAAAATTT TACAAGATAC TATTTGGAGT     600
CTATGGACTG TCTATAAAGA AGAACACGGT GAAAACTTCG GCGACTAC                  648
```

(2) INFORMATION FOR SEQ ID NO:10:

(i) SEQUENCE CHARACTERISTICS:
(A) LENGTH: 215 amino acids
(B) TYPE: amino acid
(C) STRANDEDNESS: single
(D) TOPOLOGY: linear (i i) MOLECULE TYPE: protein (x i) SEQUENCE DESCRIPTION: SEQ ID NO:10:

| Lys | Leu | Ile | Asn | Arg | Gln | Asp | Glu | Lys | Tyr | Asn | Leu | Glu | Leu | Leu | Lys |
|---|---|---|---|---|---|---|---|---|---|---|---|---|---|---|---|
| 1 | | | | 5 | | | | | 10 | | | | | 15 | |

| Asp | Leu | Gly | Leu | Asp | Val | Lys | Asn | Tyr | Leu | Phe | Asp | Ile | Glu | Ala | Gly |
|---|---|---|---|---|---|---|---|---|---|---|---|---|---|---|---|
| | | | 20 | | | | 25 | | | | | 30 | | | |

| Ile | Lys | Val | Asn | Glu | Tyr | Ile | Glu | Ser | Ala | Ile | Thr | Leu | Asp | Ser | Thr |
|---|---|---|---|---|---|---|---|---|---|---|---|---|---|---|---|
| | | 35 | | | | 40 | | | | 45 | | | | | |

| Ser | Ile | Lys | Thr | Lys | Phe | Asp | Lys | Ile | Ala | Pro | Ile | Leu | Gln | Thr | Ile |
|---|---|---|---|---|---|---|---|---|---|---|---|---|---|---|---|
| | 50 | | | | | 55 | | | | | 60 | | | | |

| His | Thr | Ser | Ala | Lys | Glu | Leu | Arg | Gly | Glu | Phe | Ala | Pro | Phe | Glu | Glu |
|---|---|---|---|---|---|---|---|---|---|---|---|---|---|---|---|
| 65 | | | | | 70 | | | | | 75 | | | | | 80 |

| Ile | Lys | Lys | Tyr | Glu | Ser | Leu | Ile | Glu | Glu | Gln | Ile | Pro | Tyr | Ala | Asn |
|---|---|---|---|---|---|---|---|---|---|---|---|---|---|---|---|
| | | | | 85 | | | | | 90 | | | | | 95 | |

| Tyr | Glu | Ser | Val | Arg | Asn | Ala | Val | Phe | Ser | Leu | Glu | Lys | Arg | Leu | Ala |

|     | 100 |     |     |     |     | 105 |     |     |     |     | 110 |     |     |
| --- | --- | --- | --- | --- | --- | --- | --- | --- | --- | --- | --- | --- | --- |

Asp Leu Gly Val Asp Arg Lys Ser Cys His Ile Asp Leu Val Pro Glu
                115                 120                 125

Asn Phe Ile Glu Ser Pro Gln Gly Arg Leu Tyr Ile Asp Trp Glu Tyr
130                         135                 140

Ser Ser Met Asn Asp Pro Met Trp Asp Leu Ala Ala Leu Phe Leu Glu
145                     150                 155                     160

Ser Glu Phe Thr Ser Gln Glu Glu Glu Thr Phe Leu Ser His Tyr Glu
                165                 170                 175

Ser Asp Gln Thr Pro Val Ser His Glu Lys Ile Ala Ile Tyr Lys Ile
                180                 185                 190

Leu Gln Asp Thr Ile Trp Ser Leu Trp Thr Val Tyr Lys Glu Glu His
            195                 200                 205

Gly Glu Asn Phe Gly Asp Tyr
210                 215

(2) INFORMATION FOR SEQ ID NO:11:

(i) SEQUENCE CHARACTERISTICS:
        (A) LENGTH: 56 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:11:

Cys His Ile Asp Leu Val Pro Glu Asn Phe Ile Glu Ser Pro Gln Gly
1               5                   10                  15

Arg Leu Tyr Leu Ile Asp Trp Glu Tyr Ser Ser Met Asn Asp Pro Met
            20                  25                  30

Trp Asp Leu Ala Ala Leu Phe Leu Glu Ser Glu Phe Thr Ser Gln Glu
            35                  40                  45

Glu Glu Thr Phe Leu Ser His Tyr
            50                  55

(2) INFORMATION FOR SEQ ID NO:12:

(i) SEQUENCE CHARACTERISTICS:
        (A) LENGTH: 55 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:12:

Cys His Asn Asp Leu Val Pro Glu Asn Met Leu Leu Gln Asp Asp Arg
1               5                   10                  15

Leu Phe Phe Ile Asp Trp Glu Tyr Ser Gly Leu Asn Asp Pro Leu Phe
            20                  25                  30

Asp Ile Ala Thr Ile Ile Glu Glu Ala His Leu Ser Lys Glu Ala Ala
            35                  40                  45

Asp Phe Leu Leu Glu Thr Tyr
            50                  55

(2) INFORMATION FOR SEQ ID NO:13:

(i) SEQUENCE CHARACTERISTICS:
        (A) LENGTH: 40 amino acids
        (B) TYPE: amino acid
        (C) STRANDEDNESS: single (D) TOPOLOGY: linear (ii) MOLECULE TYPE: protein (xi) SEQUENCE DESCRIPTION: SEQ ID NO:13:

Glu Ser Asp Gln Thr Pro Val Ser His Glu Lys Ile Ala Ile Tyr Lys
1               5                   10                  15

Ile Leu Gln Asp Thr Ile Trp Ser Leu Trp Thr Val Tyr Lys Glu Glu
                20                  25                  30

Xaa Gly Glu Asn Phe Gly Asp Tyr
            35                  40

(2) INFORMATION FOR SEQ ID NO:14:

(i) SEQUENCE CHARACTERISTICS:
    (A) LENGTH: 40 amino acids
    (B) TYPE: amino acid
    (C) STRANDEDNESS: single
    (D) TOPOLOGY: linear (ii) MOLECULE TYPE: protein (xi) SEQUENCE DESCRIPTION: SEQ ID NO:14:

His Lys Thr Glu Phe Gln Ile Ala His Lys Arg Leu Lys Ile His Arg
1               5                   10                  15

Phe Cys Gln Asn Val Leu Trp Phe Leu Trp Thr Lys Val Lys Glu Glu
                20                  25                  30

His Gly Glu Asn Phe Gly Asp Tyr
            35                  40

(2) INFORMATION FOR SEQ ID NO:15:

(i) SEQUENCE CHARACTERISTICS:
    (A) LENGTH: 41 amino acids
    (B) TYPE: amino acid
    (C) STRANDEDNESS: single
    (D) TOPOLOGY: linear (ii) MOLECULE TYPE: protein (xi) SEQUENCE DESCRIPTION: SEQ ID NO:15:

Cys His Ile Asp Leu Val Pro Glu Asn Phe Ile Glu Ser Pro Gln Gly
1               5                   10                  15

Arg Leu Tyr Leu Ile Asp Trp Glu Tyr Ser Ser Met Asn Asp Pro Met
                20                  25                  30

Trp Asp Leu Ala Ala Leu Phe Leu Glu
            35                  40

(2) INFORMATION FOR SEQ ID NO:16:

(i) SEQUENCE CHARACTERISTICS:
    (A) LENGTH: 41 amino acids
    (B) TYPE: amino acid
    (C) STRANDEDNESS: single
    (D) TOPOLOGY: linear (ii) MOLECULE TYPE: protein (xi) SEQUENCE DESCRIPTION: SEQ ID NO:16:

Cys His His Asp Ser Thr Pro Asp Asn Leu Val Tyr Thr Pro Lys Lys
1               5                   10                  15

Gln Val Val Leu Ile Asp Phe Glu Trp Ser Cys Val Asp Asn Pro Tyr
                20                  25                  30

Tyr Glu Ile Ala Asn Ile Ile Arg Glu
            35                  40

(2) INFORMATION FOR SEQ ID NO:17:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:17:

Phe Leu Ile Met Val Met Tyr
    1                  5

(2) INFORMATION FOR SEQ ID NO:18:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:18:

TGYCAYATYG AYTTRGTNCC WGARAAY          27

(2) INFORMATION FOR SEQ ID NO:19:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:19:

RTARTCRCCR AARTTYTCWC CNTGYTCYTC YTT          33

COMPOSITIONS AND METHODS FOR TREATMENT OF INFECTION CAUSED BY *HAEMOPHILUS INFLUENZAE* AND *STREPTOCOCCUS PNEUMONIAE*

GOVERNMENT SUPPORT

This invention was supported in part by a grant from the U.S. Government (Public Health Service Grant No. AI38446) and the U.S. Government may therefore have certain rights in the invention.

CROSS REFERENCE TO RELATED APPLICATIONS

This application claims priority under 35 U.S.C. § 119(e) to U.S. Provisional application Ser. No. 60/026,940, filed on Sep. 23, 1996.

FIELD OF THE INVENTION

The field of the invention is bacterial enzymes as targets for antibiotic therapy.

Background of the Invention

*Haemophilus influenzae* (*H. influenzae*) is responsible for a variety of infections in humans including respiratory tract infections, systemic infections and purulent meningitis. Type b *H. influenzae* strains are primary pathogens that occasionally multiply and spread into the deeper tissues beyond the nasopharynx. This invasion may involve inflammation and edema of the epiglottis or facial and neck tissues. Bacteremia, which is common once the organisms spread beyond the nasopharynx, is likely the mechanism for entry of bacteria into the central nervous system and for metastatic infections at distant sites such as bones and joints. Host factors probably determine whether meningitis, arthritis, or more local infection results. Systemic spread is typical only for encapsulated *H. influenzae* strains and over 90% of invasive strains are type b. *H. influenzae* is reviewed in Sherris (1990, Medical Microbiology, Elsevier, New York, pp. 401–408).

There is now available a vaccine directed against *H. influenzae* type b, which vaccine is effective in preventing invasiveness of this organism in humans. However, non-typable strains of *H. influenzae* also cause significant infection in humans, and the ability to cause respiratory tract infection is largely unaffected by prior administration of the available type b vaccine. Thus, there remains an acute need for the development of therapies, such as antibiotics, which are effective against non-typable strains of *H. influenzae*.

Carrier rates for *H. influenzae* as high as 80% have been found in children and are commonly 20–50% in healthy adults. Although infection by *H. influenzae* occurs primarily in children, evidence is accumulating that adult infections are becoming more frequent. The reason for this trend is not known, but changes in the incidence of infection, virulence of the organism, and the impact of antimicrobiotic usage on development of immunity are likely factors.

The surface glycolipid or lipopolysaccharide (LPS) of *H. influenzae* consists of lipid A, an inner core of a single phosphorylated 2-keto-3-deoxy-octulosonic acid (KDO) linked to three heptose molecules, and an outer core consisting of a heteropolymer of glucose and galactose (Zamze et al., 1987, J. Gen. Microbiol. 133:1443–1451; Phillips et al., 1993, Biochemistry 32:2003–2012). *H. influenzae* LPS lacks the multiple O-linked saccharide units characteristic of the smooth LPS of the enterobacteriaceae. The complete structure of the glycolipid has not been resolved because of marked intra- and interstrain heterogeneity in the composition and linkage of saccharide units in the outer core (Inzana, 1983, J. Infect. Dis. 148:492–499; Kimura et al., 1986, Infect. Immun. 51:69–79).

There is high frequency ($10^{-2}$ to $10^{-3}$/generation), spontaneous, reversible gain and loss (phase variation) of oligosaccharide epitopes expressed by genes in three chromosomal loci of *H. influenzae*, lic1, lic2 and lic3 (Weiser et al., 1990, J. Bacteriology 172:3304–3309). A common feature in each of the three loci is the presence of multiple tandem repeats of the tetramer 5'-CAAT-3' within the coding region of the first gene (Weiser et al., 1989, Cell 59:657–665). Slipped-strand mispairing within this highly repetitive sequence shifts the 5' end of the gene into or out of frame with the remainder of the open reading frame thus creating a translational switch.

The *H. influenzae* genome has been sequenced in its entirety and an analysis of the sequence has revealed that the presence of highly repetitive sequences which generate molecular switches are a common feature of many genes, especially those involved in the expression of cell surface components (Fleischmann et al., 1995, Science 269:497–512). Regarding the lic loci, downstream genes are associated with expression of oligosaccharide epitopes identified by the monoclonal antibody (MAb) 4C4 in the case of lic2, and 12D9 in the case of lic1 ((Weiser et al., 1990, supra; Gulig, et al, 1987, Infect. Immun. 55:513–520). Specific saccharide structures controlled by these loci are known only in the case of lic2 and lic3; lic2 is required for expression of the structure Galα(1–4)βGal, while lic3 contains galactose epimerase, galE (High et al., 1993, Mol. Microbiol. 9:1275–1282; Maskell et al., 1991, Mol. Microbiol. 5:1013–1022).

In contrast, lic1, which is present in all strains of a representative survey of *H. influenzae* isolates, has not been associated with any specific oligosaccharide structure (Weiser et al., 1990, supra). Defined mutations in lic1, which comprises four genes (licA, B, C and D), eliminate expression of the epitope defined by the MAb 12D9, but have little apparent effect on LPS size (Weiser, 1993, J. Infect. Dis. 168:672–680).

Phase-variable LPS structures may contribute to the pathogenesis of *H. influenzae* (Maskell et al., 1991, supra; Zwahlen et al., 1986, Microbial. Pathogenesis 1:465–473; Kimura et al., 1987, Infect. Immun. 55:1979–1986). In a virulent, serotype b clinical isolate, a lic1–lic2 negative mutant was capable of colonizing the nasopharynx in an infant rat model of *H. influenzae* carriage, but was relatively deficient in causing septicemia following intranasal inoculation (Weiser et al., 1990, Infect. Immun. 58:3455–3457).

*Streptococcus pneumoniae* (*S. pneumoniae*) is a major human respiratory pathogen which is the causative agent of both acute bacterial pneumonia and acute purulent meningitis in humans. This organism efficiently colonizes the mucosal surface of the human nasopharynx, which colonization is the initial step in the pathogenesis of respiratory tract infection (Tuomanen et al., 1995, New Engl. J. Med. 332:1280–1284). *S. pneumoniae* is highly adapted to its human host since natural infection of other host species, even in the carrier state, is unusual. One important factor in the ability of this organism to establish a presence on mucosal surfaces is its effective evasion of local host defenses. *S. pneumoniae* is a common cause of pneumonia in communities, such as a hospital or a home. In approximately 20% of infected individuals, bacteremia is observed.

S. pneumoniae requires choline for growth. This organism takes choline from the growth medium and incorporates it into cell wall components in the form of choline phosphate or phosphorylcholine (ChoP). The cell wall component into which choline is incorporated in this organism is cell wall associated teichoic acid. In addition, choline is incorporated into the membrane anchored glycolipid, lipoteichoic acid (Fisher et al., 1993, Eur. J. Biochem. 215:851–857; Mosser et al., 1970, J. Biol. Chem. 245:287–298).

Treatment of infection by H. influenzae generally involves administration of antibiotics such as ampicillin, amoxicillin, cephalosporins, chloramphenicol, tetracycline, aminoglycosides and sulfonamides. However, the emergence of drug resistant strains of H. influenzae accentuates the need for the identification of new antibiotic targets in H. influenzae and for the development of antibiotics directed against those targets which are capable of inhibiting the growth and/or pathogenesis of H. influenzae in the human host.

Similarly, treatment of infection by S. pneumoniae also involves administration of antibiotics such as penicillin. However, given the recent emergence of penicillin-resistant and mulitdrug-resistant strains of S. pneumoniae, other antibiotics such as erythromycin are also prescribed (Klugman, 1990, Clin. Microbiol. Rev. 3:171–196). The fact that strains of this organism have evolved which are resistant to antibiotic therapy accentuates the need for prevention by vaccination of S. pneumoniae-induced disease, for the identification of new antibiotic targets in S. pneumoniae, and for the development of antibiotics directed against those targets which are capable of inhibiting the growth and/or pathogenesis of S. pneumoniae in the human host.

Both H. influenzae and S. pneumoniae are the causative agents of very similar respiratory diseases. The development of an antibacterial compound or compounds which are capable of acting on either of these organisms may save essential time in treatment of an individual having a serious disease caused by either organism.

The present invention provides a means for identification of compounds capable of inhibiting growth of bacteria such as H. influenzae or S. pneumoniae, and other bacteria, and thus satisfies the aforementioned needs.

SUMMARY OF THE INVENTION

The invention relates to a method of identifying a compound capable of disrupting the addition of choline onto a bacterial cell surface component comprising incubating a sample of bacteria in a solution containing choline in the presence or absence of a test compound, and assessing the effect of the test compound on the addition of choline onto the bacterial cell surface component, wherein a lower level of choline on the cell surface component in the presence of the test compound, compared with the level of choline on the cell surface component in the absence of the test compound, is an indication that the test compound inhibits the addition of choline onto the cell surface component.

In one aspect, cell surface component is a cell wall component. Preferably, the cell surface component is selected from the group consisting of lipopolysaccharide, teichoic acid, lipoteichoic acid, protein and glycoprotein.

In another aspect, the bacteria are selected from the group consisting of H. influenzae and S. pneumoniae.

The invention also relates to a method of identifying a compound capable of disrupting the addition of choline onto a bacterial cell surface component comprising incubating a bacterial extract in a solution containing choline in the presence or absence of a test compound, and assessing the effect of the test compound on the addition of choline onto the bacterial cell surface component, wherein a lower level of choline on the cell surface component in the presence of the test compound, compared with the level of choline on the cell surface component in the absence of the test compound, is an indication that the test compound inhibits the addition of choline onto the cell surface component.

In one aspect, the cell surface component is a cell wall component bing preferably selected from the group consisting of lipopolysaccharide, teichoic acid, lipoteichoic acid, protein and glycoprotein.

In another aspect, the bacterial extract is obtained from bacteria selected from the group consisting of H. influenzae and S. pneumoniae.

Also included in the invention is a method of identifying a compound capable of disrupting the addition of choline onto a bacterial cell surface component comprising incubating an isolated preparation of a bacterial choline kinase in a solution containing choline in the presence or absence of a test compound, and assessing the effect of the test compound on the addition of choline onto the bacterial cell surface component, wherein a lower level of choline on the cell surface component in the presence of the test compound, compared with the level of choline on the cell surface component in the absence of the test compound, is an indication that the test compound inhibits the addition of choline onto the cell surface component.

In one aspect the cell surface component is a cell wall component being preferably selected from the group consisting of lipopolysaccharide, teichoic acid, lipoteichoic acid, protein and glycoprotein.

In another aspect, the bacterial choline kinase is elected from the group consisting of H. influenzae and S. pneumoniae choline kinase.

The invention also includes a compound capable of disrupting the addition of choline onto a bacterial cell surface component identified by the methods of the invention.

BRIEF DESCRIPTION OF THE DRAWINGS

FIG. 1 is a photograph of a Western blot of proteins derived from H. influenzae and Streptococcus pneumoniae (S. pneumoniae). Phosphorylcholine-containing molecules were detected using the MAb, TEPC-15, on whole-cell lysates separated on 15% SDS-PAGE. Lane 1: S. pneumoniae; Lane 2: S. pneumoniae (lipoteichoic acid); Lane 3: H. influenzae strain Eagan; and Lane 4: H. influenzae strain Rd$^-$. Size markers are protein standards in kilodaltons.

FIG. 4 are photographs of a series of immunoblots of bacterial colonies.

FIG. 6 depicts the sequence similarity between *H. influenzae* LicA and eukaryotic choline kinases. The region of *H. influenzae* LicA from amino acid 222 through 262 was compared to choline kinases obtained from *Saccharomyces cerevisiae, Caenorhabditis elegans,* and *Rattus norvegicus* rat liver. In the case of *S. cerevisiae* choline kinase, the asterisk denotes 41 amino acids that were deleted in order to optimize the alignment. Amino acids conforming to the consensus sequence of phosphotransferases and protein kinases described by Brenner are indicated in bold (Brenner, 1987, supra). Amino acids identical to those of LicA of *H. influenzae* are indicated (|). Also shown is the sequence comparison of the same region of LicA from *H. influenzae* and the corresponding region of a gene of unknown function identified in *Mycoplasma hominis.* [SEQ ID NOS: 1–8, proceeding from the top to the bottom of the figure].

FIG. 9 is the DNA sequence of approximately two thirds of the *S. pneumoniae* strain P376 choline kinase gene and the accompanying deduced amino acid sequence thereof [SEQ ID NOS: 9–10].

FIG. 10 depicts the sequence similarity between *H. influenzae* LicA (Hi) and a choline kinase identified in *S. pneumoniae* (Sp) and the sequence similarity between *S. pneumoniae* and that identified in *Mycoplasma pneumoniae* (Mp) [SEQ ID NOS 11–16].

FIG. 11 is a summary of a comparison of *H. influenzae* choline kinase and *S. pneumoniae* choline kinase using the BLAST program.

DETAILED DESCRIPTION OF THE INVENTION

Figure 2A:
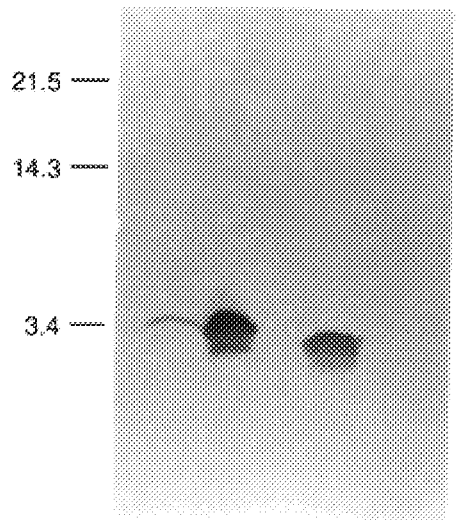
FIG. 2 are photographs of a Western blot (FIG. 2A) and a silver stained gel (FIG. 2B) of purified LPS obtained from phosphorylcholine phase-variants. MAb TEPC-15 reactive and non-reactive colonies were grown separately to mid-log phase. The LPS was extracted and equal quantities were separated on 16.6% tricine SDS-PAGE gel and immunoblotted with TEPC-15 (FIG. 2A) or silver stained (FIG. 2B). Lane 1: Eagan (TEPC-15 non-reactive); Lane 2: Eagan (TEPC-15 reactive); Lane 3: Rd$^-$ (TEPC-15 reactive); Lane 4: Rd$^-$ (TEPC-15 non-reactive). The presence (+) or absence (−) of a quaternary amine structure in the purified LPS as determined by reactivity with Dragondorff's reagent is indicated below. Size markers are protein standards in kilodaltons.

It has been discovered in the present invention that two bacterial species, *H. influenzae* and *S. pneumoniae,* encode a choline kinase which phosphorylates choline to choline phosphate (ChoP), for incorporation of the same into cell wall structures.

While not wishing to be bound by any theory, it is believed that the addition of choline to cell wall structures in either species of bacteria enhances the invasive capacity of the organism thereby exacerbating serious disease caused by either organism.

In the case of *H. influenzae,* it has been discovered that a group of genes known as lic genes encode enzymes which facilitate the addition of choline to cell surface components in bacteria. In particular, the function of the products of some of the lic genes of *H. influenzae* has been discovered to facilitate the transfer of choline from the bacterial growth medium onto LPS in *H. influenzae.* More particularly, the lic1 locus of the *H. influenzae* genome, comprising the genes licA, licB, licC and licD, has been discovered to facilitate choline addition to *H. influenzae* LPS. Even more particularly, it has been discovered that the product of the licA gene is a choline kinase.

The function of lic genes in *H. influenzae* has been largely a mystery until the discovery of the present invention. Moreover, the function of lic genes encoded by other bacteria is not well understood. Thus, it now becomes clear, given the discovery of the present invention, that lic genes in bacteria are involved in choline addition to cell surface components. Such cell surface components include, but are not limited to, LPS in gram negative bacteria and teichoic acid and lipoteichoic acid in gram positive bacteria. In addition, proteins and glycoproteins may also have choline added to them in some bacteria. Bacteria having choline on their cell surface include, but are not limited to, *H. influenzae, S. pneumoniae, Mycoplasma pneumoniae, Neisseria gonorrhea, Neisseria meningiditis* and *Pseudomonas aeruginosa.* Genes which are directly involved in the transfer of choline onto bacterial cell surfaces are termed "lic" genes.

The invention includes a method of identifying a compound capable of disrupting the addition of choline onto a bacterial cell surface component. The method involves incubating a sample of bacteria, bacterial extract or an isolated preparation of any one or more of proteins encoded by bacterial lic genes, in a solution containing choline in the presence or absence of the test compound, and assessing the effect of the test compound on the addition of choline onto the bacterial cell surface components. A lower level of choline on the cell surface component in the presence of the test compound, compared with the level of choline on the cell surface component in the absence of the test compound, is an indication that the test compound inhibits the addition of choline onto the cell surface component.

Preferably, the cell surface component is LPS, teichoic acid or lipoteichoic acid and the bacterium is *H. influenzae, S. pneumoniae, Mycoplasma pneumoniae, Neisseria gonnorhea, Neisseria meningiditis,* or *Pseudomonas aeruginosa.*

The invention also includes a compound having an activity which inhibits the addition of phosphate onto choline. Compounds so identified using the method of the invention may be tested further, as described herein, for activity which affects the growth or the pathogenicity of bacteria in humans.

It has been discovered in the present invention that choline is added to the lipopolysaccharide (LPS) of *H. influenzae* as phosphorylcholine (ChoP). It has been further discovered that the substitution of choline onto LPS is mediated by genes located in lic1 locus of *H. influenzae.* Thus, substitution of choline onto *H. influenzae* requires expression of licA and likely licB, licC and licD. The licA gene contains the molecular switch (5'-CAAT-3')n and is translated into a protein having similarity with eukaryotic choline kinase. The substitution of choline onto LPS contributes to phase variation of *H. influenzae* and therefore survival of this organism in the respiratory tract of humans.

It has also been discovered in the present invention that *S. pneumoniae* encodes a choline kinase having sequence similarity to that of *H. influenzae* LicA choline kinase. Thus, the methods of the invention which are described with respect to the use and treatment of *H. influenzae* are equally applicable to the use and treatment of *S. pneumoniae.*

The invention includes a method of identifying a compound having antibiotic activity by screening test compounds for their ability to affect the expression or activity of any one of the *H. influenzae* lic1 locus genes described herein or of the *S. pneumoniae* choline kinase also described herein.

By "antibiotic activity" as used herein, is meant a compound which is capable of destroying or inhibiting the growth of bacteria or which is capable of inhibiting the pathogenesis, i.e., the disease-causing capacity, of a microorganism. The term, as used herein, should not be construed as being limited solely to activity directed against either or both of *H. influenzae* and *S. pneumoniae.* Rather, compounds having antibiotic activity directed against either or both of these organisms may be tested for antibiotic activity directed against any other type of bacterium to determine if such a bacterium also exhibits sensitivity to the compound.

In one aspect of the method of the invention, a compound is assessed for antibiotic activity by assessing the effect of the compound on the addition of choline to *H. influenzae.* In this instance, the test compound is added to an assay mixture designed to measure choline addition to *H. influenzae* LPS. The assay mixture may comprise a mixture of cells which express lic1 genes (either individually or in various combinations), [$^3$H]-choline, a buffer solution suitable for optimal addition of choline onto LPS, and the test compound. Controls may include the assay mixture without the test compound and the assay mixture having the test compound and cells which do not express the appropriate lic1 genes. The mixture is incubated for a predetermined length of time and at a temperature suitable for the addition of choline to LPS as described herein, whereupon the reaction is stopped and the presence or absence of choline on LPS is assessed also as described herein.

Alternatively, the assay mixture may comprise a cell free sample, for example, a cell-free extract comprising any one or more of LicA, LicB, LicC and LicD, or an isolated preparation of any one or more of LicA, LicB, LicC and LicD, choline, LPS, a buffer and the test compound. Incubation of the assay mixture is conducted as described herein and the addition of choline to LPS is assessed also as described herein.

It will be appreciated that the above-described assay is equally applicable to the use of *S. pneumoniae* in place of *H. influenzae,* wherein the addition of choline to teichoic acid or lipoteichoic acid is measured in place of LPS.

In the case of *S. pneumoniae,* the assay mixture may comprise a cell free sample comprising *S. pneumoniae* choline kinase, or an isolated preparation of the same, choline, teichoic acid or lipoteichoic acid, a buffer and the test compound. Incubation of the assay mixture is conducted as described herein and the addition of choline to teichoic acid or lipoteichoic acid is assessed also as described herein.

Compounds which inhibit the addition of choline onto LPS, teichoic acid or lipoteichoic acid may be easily identified in the assay by assessing the amount of choline which is added to these cell wall components in the presence or absence of the test compound. A lower level or the absence of choline on the subject cell wall component in the presence of the test compound compared with the level of choline in the absence of the test compound in the assay mixture is an indication that the test compound inhibits the addition of choline onto the cell wall component.

The presence or absence of choline on LPS is assessed by incubating *H. influenzae,* or a cell extract, or an isolated preparation of a protein obtained therefrom, in the presence of choline-containing medium, wherein the choline is labeled with a detectable label, either a radioactive or other label. Incorporation of the label into LPS is determined by measuring the amount of radioactivity (or color, if appropriate) in LPS extracted from the cells. The presence of quaternary amines, including choline, on LPS is assessed using a colorimetric reagent such as Dragendorff's reagent on samples which are spotted onto nitrocellulose sheets, dried and then reacted with the reagent.

The presence of choline on LPS may also be assessed using an antibody, preferably, a monoclonal antibody specific for phosphorylated choline, such as, but not limited to the monoclonal antibody TEPC-15, as described herein.

The assay mixture may also comprise a preparation of LPS, LicA, choline which is labeled, preferably by radioactive label, a source of phosphate suitable for addition of the same onto choline, a buffer suitable for the activity of LicA, and optionally, the test compound. Since LicA has been discovered in the present invention to possess choline kinase activity, the assay may therefore be designed to assess the effect of a test compound on the addition of phosphate to choline by measuring the amount of choline phosphate which is generated following incubation of the assay mixture in the presence or absence of the test compound. A lower level of choline phosphate in the presence of the test compound compared with the level of choline phosphate in the absence of the test compound, is an indication that the test compound has an effect on the addition of phosphate onto choline. Compounds which have an effect on choline kinase activity may then be tested further for antibiotic activity in the methods described herein.

The presence or absence of choline on teichoic acid, lipoteichoic acid or other cell surface components such as proteins and glycoproteins, is assessed using a monoclonal antibody, such as, but not limited to, TEPC-15 as described herein, which capable of recognizing the same, in conjunction with Western blotting or other known immunologically-based assays.

The methods of the invention are not limited by the type of test compound which may be used in the assay. The test compound may thus be a synthetic or naturally occurring molecule which may comprise a peptide or peptide-like molecule, or it may be any other molecule, either small or large, which is suitable for testing in the assay. The test compound may also be an antibody directed against any one of the bacterial lic gene products.

Compounds which inhibit the addition of choline onto LPS in the in vitro assay, or which inhibit choline kinase activity as described herein, may also be tested for antibiotic activity directed against *H. influenzae* in an in vivo animal model. The spectrum of illnesses caused by *H. influenzae* is a reflection of its ability to survive in various ecological niches in the human host. The organism colonizes the respiratory tract in humans causing disease in both the upper and lower respiratory tracts and in addition, is one of the leading causes of bacterial meningitis in humans (Moxon et al. 1991, Rev. Inf. Dis. 13(suppl.):s518).

The infant rat model may be used to assess whether a compound has antibiotic activity directed against *H. influenzae* in vivo (Weiser, 1993, supra). Colonization of the mucosal surface of the nasopharynx by *H. influenzae* in the presence or absence of the test compound is assessed. Since, as noted herein, the ability of *H. influenzae* to colonize the nasopharynx is derived at least in part from its ability to incorporate choline onto LPS, it is predicted that compounds which inhibit incorporation of choline onto LPS will have an effect on *H. influenzae* colonization of the nasopharynx.

Briefly, an amount of *H. influenzae*, generally about 10 $\mu$l of phosphate buffered saline (PBS)-washed mid log phase organisms at $10^7$ colony forming units per ml are inoculated into the left anterior naris of the animal. Colony counts are performed to ensure that the inocula are of the desired density and phenotype. The nasopharynx is cultured for the presence of viable *H. influenzae* by the slow instillation of 20 to 40 $\mu$l of sterile PBS into the left naris and withdrawal of the initial 10 $\mu$l from the right naris. This procedure ensures that the fluid has passed through the nasopharynx. The quantity of organisms recovered is then assessed in any well known culture assay for *H. influenzae*.

The effect of the test compound on colonization of the nasopharynx by *H. influenzae* is evaluated by comparing the degree of colonization of the nasopharynx in animals which have been administered the test compound with the degree of colonization in animals which have not been administered the test compound, wherein a lower degree of colonization in animals administered the test compound is an indication that the test compound inhibits colonization of the nasopharynx by *H. influenzae*.

The invasive capability of *H. influenzae* may also be measured in the infant rat model. Essentially, bacteria which have entered the blood stream following inoculation of the nasopharynx are detected by culturing the same in a sample of blood obtained from the animal. Again, the effect of the test compound on the invasive capacity of *H. influenzae* is assessed by comparing the number of organisms found in the blood stream in animals which have been administered the test compound with the number of organisms in the blood stream in animals which have not been administered the test compound, wherein a lower number of organisms in the blood stream of animals administered the test compound is an indication that the test compound has an effect on the invasive capacity of *H. influenzae*.

The virulence of *H. influenzae* is also assessed following the procedures described in Weiser (1993, supra). Essentially, 100 $\mu$l of PBS-washed mid log phase bacteria at $10^3$ colony forming units per ml are inoculated into the animal intraperitoneally. The survival time of the animals is recorded and the differences in median survival time between groups may be analyzed by the Mann-Whitney U test (two-tailed). Differences in the overall survival rate between groups may be analyzed by the $x^2$ test (two tailed).

The effect of the test compound on the virulence of *H. influenzae* is assessed by comparing the survival rates of animals which have been administered the test compound with the survival rate of animals which have not been administered the test compound, wherein a higher survival rate of animals administered the test compound is an indication that the test compound has an effect on the virulence of *H. influenzae*.

To determine the effect of a test compound on colonization of the mucosal surface or on invasiveness and/or virulence of *H. influenzae*, the test compound is administered to the animals either prior to, at the time of, or after inoculation of the animals with *H. influenzae*. The test compound may be administered directly into the nasopharynx, or may be administered by any other route including any one of the traditional modes (e.g., orally, parenterally, transdermally or transmucosally), in a sustained release formulation using a biodegradable biopolymer, or by on-site delivery using micelles, gels and liposomes, or rectally (e.g., by suppository or enema). Precise formulations and dosages will depend on the nature of the test compound and may be determined using standard techniques, by a pharmacologist of ordinary skill in the art.

Compounds which inhibit *S. pneumoniae* choline kinase activity in vitro may be assessed in an in vivo animal model. There are essentially two types of in vivo models in which a compound may be tested for antibiotic activity directed against *S. pneumoniae*. In the first model, colonization of the mucosal surface of the nasopharynx by *S. pneumoniae* in the presence or absence of the test compound is assessed. Since, as noted herein, the ability of *S. pneumoniae* to survive in the nasopharynx is derived at least in part from its ability to evade the host immune response, it is predicted that compounds which inhibit *S. pneumoniae* choline kinase will have an effect on *S. pneumoniae* colonization of the nasopharynx.

Measurement of colonization of the mucosal surface of the nasopharynx by *S. pneumoniae* may be conducted in an animal model essentially as described in Weiser et al. (1994, supra).

To assess colonization, briefly, an amount of *S. pneumoniae*, generally about 10 $\mu$l of phosphate buffered saline (PBS)-washed mid log phase organisms adjusted to the desired density, is inoculated into the left anterior naris of the animal. Colony counts are performed to ensure that the inocula are of the desired density and phenotype. The nasopharynx is cultured for the presence of viable *S. pneumoniae* by the slow instillation of 20 to 40 $\mu$l of sterile PBS into the left naris and withdrawal of the initial 10 $\mu$l from the right naris. This procedure ensures that the fluid has passed through the nasopharynx. The quantity of organisms recovered is then assessed in a well known culture assay.

The effect of the test compound on colonization of the nasopharynx by *S. pneumoniae* is evaluated by comparing the degree of colonization of the nasopharynx in animals which have been administered the test compound with the degree of colonization in animals which have not been administered the test compound, wherein a lower degree of colonization in animals administered the test compound is an indication that the test compound inhibits colonization of the nasopharynx by S. pneumoniae.

The invasive capability of S. pneumoniae may also be measured in the same animal model. Essentially, bacteria which have entered the blood stream following inoculation of the nasopharynx are detected by culturing the same in a sample of blood obtained from the animal. Again, the effect of the test compound on the invasive capacity of S. pneumoniae is assessed by comparing the number of organisms found in the blood stream in animals which have been administered the test compound with the number of organisms in the blood stream in animals which have not been administered the test compound, wherein a lower number of organisms in the blood stream of animals administered the test compound is an indication that the test compound has an effect on the invasive capacity of S. pneumoniae.

In a second in vivo model, the virulence of S. pneumoniae is assessed in animals as described in Berry et al. (1995, Infect. Immun. 63:1969–1974). Essentially, cultures of S. pneumoniae are diluted to a density of $2\times10^6$ colony forming units per ml, and volumes of 0.1 ml are injected intraperitoneally into groups of animals. The survival time of the animals is recorded and the differences in median survival time between groups may be analyzed by the Mann-Whitney U test (two-tailed). Differences in the overall survival rate between groups may be analyzed by the $x^2$ test (two tailed).

The effect of the test compound on the virulence of S. pneumoniae is assessed by comparing the survival rates of animals which have been administered the test compound with the survival rate of animals which have not been administered the test compound, wherein a higher survival rate of animals administered the test compound is an indication that the test compound has an effect on the virulence of S. pneumoniae.

To determine the effect of a test compound on colonization of the mucosal surface or on invasiveness and/or virulence of S. pneumoniae, the test compound is administered to the animals either prior to, at the time of, or after inoculation of the animals with S. pneumoniae. The test compound may be administered directly into the nasopharynx, or may be administered by any other route including any one of the traditional modes (e.g., orally, parenterally, transdermally or transmucosally), in a sustained release formulation using a biodegradable biopolymer, or by on-site delivery using micelles, gels and liposomes, or rectally (e.g., by suppository or enema). Precise formulations and dosages will depend on the nature of the test compound and may be determined using standard techniques, by a pharmacologist of ordinary skill in the art.

A compound which is identified in any of the above assays as having antibiotic activity directed against H. influenzae and/or S. pneumoniae may then be tested for antibiotic activity directed against a variety of other organisms, particularly those organisms which are known to or are suspected to encode and express a choline kinase. Thus, any compound which is identified as an anti-S. pneumoniae antibiotic may not only be useful for treatment of infections caused by S. pneumoniae, but may also be useful for treatment of infections caused by a variety of other bacteria and even other non-bacterial microorganisms, such as fungi and the like.

Once the test compound has been identified as having anti-H. influenzae and/or anti-S. pneumoniae activity in the assays described herein, it may be formulated so as to be suitable for administration to humans for treatment of diseases caused by either of these organisms.

Compounds which inhibit S. pneumoniae choline kinase activity in vitro or in vivo may be tested for antibiotic activity directed against S. pneumoniae in vivo in humans. The spectrum of illnesses caused by S. pneumoniae is a reflection of its ability to survive in various ecological niches in the human host. The organism resides in the nasopharynx, commonly without adverse effect on the host, but may spread locally to cause upper or lower respiratory tract infection. In some circumstances, S. pneumoniae cells may enter the blood stream from the nasopharynx via the cervical lymph nodes, leading to bacteremia and occasionally, infection of other organ systems (Weiser et al., 1994, Infect. Immun. 62:2582–2589).

Essentially, the compound is administered to the human by any one of the routes described herein, and the effect of the compound on infection by S. pneumoniae is assessed by clinical and symptomatic evaluation. Such assessment is well known to the artisan in the field of S. pneumoniae and other respiratory tract infections.

While the genes located within the lic1 locus of H. influenzae that mediate addition of choline onto LPS were initially discovered in selected strains of H. influenzae (see Table 1), the use of lic1 locus genes derived from any other H. influenzae strain are also useful in the methods of the invention. Preferably, the nucleotide sequence of any one of the licA, licB, licC and licD genes are about 50% homologous, more preferably about 70% homologous, even more preferably about 80% homologous and most preferably about 90% homologous to the known nucleotide sequences of the licA, licB, licC and licD genes, respectively, which are described herein as facilitating choline addition to LPS.

Similarly, the invention should be construed to include genes encoding choline kinase which are homologous to the S. pneumoniae choline kinase described herein. Preferably, the nucleotide sequence of a choline kinase useful in the methods of the invention is about 50% homologous, more preferably about 70% homologous, even more preferably about 80% homologous and most preferably about 90% homologous to the S. pneumoniae choline kinase sequence disclosed herein in FIG. 10.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3'ATTGCC5' and 3'TATGCG5' share 50% homology.

The genes included in the H. influenzae lic1 locus, i.e., licA, licB, licC and licD, may be isolated from any strain of H. influenzae by following the procedures described in Weiser et al. (1989, supra) which is hereby incorporated by reference herein.

For the isolation of H. influenzae lic genes, essentially, a genomic DNA library is generated from the subject H. influenzae strain and is screened for DNA fragments encompassing the lic1 locus using ordinary recombinant DNA technology described, for example, in Sambrook et al. (1989, Molecular Cloning: A Laboratory Manual, Cold Spring Harbor, New York). Individual genes located within the lic1 locus are then subcloned following the procedures described in Weiser et al. (1989, supra).

To determine whether subclones so selected actually encode a lic1 locus gene, the nucleotide sequence of the subcloned DNA is obtained. The putative amino acid sequence encoded by the DNA is deduced and this sequence is then compared with the amino acid sequence of the appropriate lic1 locus gene. In addition, the gene encoding the putative lic1 locus gene may be cloned into an expression vector and the expressed protein may be identified immunologically or by measurement of the appropriate enzymatic activity following the procedures described herein for identification of *H. influenzae* licA, licB, licC and licD.

An "isolated nucleic acid", as used herein, refers to a nucleic acid sequence, segment, or fragment which has been purified from the sequences which flank it in a naturally occurring state, e.g., a DNA fragment which has been removed from the sequences which are normally adjacent to the fragment e.g., the sequences adjacent to the fragment in a genome in which it naturally occurs. The term also applies to nucleic acids which have been substantially purified from other components which naturally accompany the nucleic acid, e.g., RNA or DNA or proteins which naturally accompany it in the cell. The term therefore includes, for example, a recombinant DNA which is incorporated into a vector; into an autonomously replicating plasmid or virus; or into the genomic DNA of a prokaryote or eukaryote; or which exists as a separate molecule (e.g, as a cDNA or a genomic or cDNA fragment produced by PCR or restriction enzyme digestion) independent of other sequences. It also includes a recombinant DNA which is part of a hybrid gene encoding additional polypeptide sequence.

The invention also includes the use of lic1 encoded proteins which are encoded by strains of *H. influenzae* other than those described herein. Preferably, the individual amino acid sequences of each of the lic1 encoded proteins of *H. influenzae* are about 70% homologous, more preferably about 80% homologous, even more preferably about 90% homologous and most preferably about 95% homologous to the respective amino acid sequences of the lic1 encoded proteins disclosed in Weiser et al. (1989, supra).

Lic1 encoded proteins of *H. influenzae* may be obtained by cloning and expressing the appropriate gene and isolating the protein so expressed using available technology in the art. Any of the lic1 proteins may be purified by following known procedures for protein purification, wherein an immunological, enzymatic or other assay is used to monitor purification at each stage in the procedure.

The isolation of other *S. pneumoniae* choline kinase genes is the same as that described herein for the isolation of the *S. pneumoniae* choline kinase gene shown in FIG. 9. Cloning and sequencing of other *S. pneumoniae* choline genes may be accomplished in a similar to that described herein for *H. influenzae* choline kinase genes.

Antibodies may be raised against any one of the lic gene products or *S. pneumoniae* choline kinase by following ordinary procedures available in the art for the generation of antibodies which are described, for example, in Harlow et al. (1988, In: Antibodies, A Laboratory Manual, Cold Spring Harbor, N.Y.).

As used herein, the term "an isolated preparation" describes a compound, e.g., a protein or polypeptide which has been separated from components which naturally accompany it. Typically, a compound is isolated when at least 10%, more preferably at least 20%, more preferably at least 50%, more preferably at least 60%, more preferably at least 75%, more preferably at least 90%, and most preferably at least 99% of the total material (by volume, by wet or dry weight, or by mole percent or mole fraction) in a sample is the compound of interest. Purity can be measured by any appropriate method, e.g., in the case of polypeptides by column chromatography, gel electrophoresis or HPLC analysis. A compound, e.g., a protein, is also considered to be isolated when it is essentially free of naturally associated components or when it is separated from the native contaminants which accompany it in its natural state.

The present invention also provides for using analogs of proteins or peptides encoded by *H. influenzae* lic1 and the *S. pneumoniae* choline kinase gene. Analogs can differ from naturally occurring proteins or peptides by conservative amino acid sequence differences or by modifications which do not affect sequence, or by both.

For example, conservative amino acid changes may be made, which although they alter the primary sequence of the protein or peptide, do not normally alter its function. Conservative amino acid substitutions typically include substitutions within the following groups:

glycine, alanine;
valine, isoleucine, leucine;
aspartic acid, glutamic acid;
asparagine, glutamine;
serine, threonine;
lysine, arginine;
phenylalanine, tyrosine.

Modifications (which do not normally alter primary sequence) include in vivo, or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Also included are polypeptides which have been modified using ordinary molecular biological techniques so as to improve their resistance to proteolytic degradation or to optimize solubility properties. Analogs of such polypeptides include those containing residues other than naturally occurring L-amino acids, e.g., D-amino acids or non-naturally occurring synthetic amino acids. The peptides of the invention are not limited to products of any of the specific exemplary processes listed herein.

In addition to substantially full length polypeptides, the present invention provides for enzymatically active fragments of the polypeptides. An *H. influenzae* lic1 encoded polypeptide is enzymatically active if it contributes to the addition of choline onto LPS in the same manner as the naturally encoded protein in the assays described below. A *S. pneumoniae* encoded choline kinase polypeptide is enzymatically active if it contributes to the addition of choline onto teichoic acid and/or lipoteichoic acid in the same manner as the naturally encoded protein in the assays described below.

As used herein, the term fragment, as applied to a polypeptide, will ordinarily be at least about twenty contiguous amino acids, typically at least about fifty contiguous amino acids, more typically at least about seventy continuous amino acids, usually at least about one hundred contiguous amino acids, preferably at least about five hundred continuous amino acids, more preferably at least about one thousand contiguous amino acids, and most preferably at least about one thousand two hundred to about one thousand nine hundred or more contiguous amino acids in length.

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Bacterial Strains, Media, and Chemicals

*H. influenzae* strains used in the experiments described herein are shown in Table 1. *H. influenzae* strains were grown in brain heart infusion (BM) broth supplemented with 1.5% Fildes enrichment with or without 1% agar (Difco Laboratories, Detroit, Mich.). *S. pneumoniae* strain Rx6 was grown as described as was *S. pneumoniae* strain P376, the latter being used for the isolation of the *S. pneumoniae* choline kinase gene (Weiser et al., 1994, Infect. Immun. 62:2582–2589). Lipoteichoic acid was obtained following the method of Fischer et al. (1983, Eur. J. Biochem. 133:523–530). Chemicals were purchased from Sigma Chemical Co. (St. Louis, Mo.) unless otherwise specified.

126:109–117). LPS was visualized using the modified silver stain described by Hitchcock et al. (1983, J. Bacteriol. 154:269–277).

Choline Incorporation and Detection

*H. influenzae* was radiolabeled by adding radioactive choline (New England Nuclear Co, Boston, Mass.) to growth medium (final concentration 0.5 $\mu$Ci/ml). *H. influenzae* was grown to an $OD_{620}$ of 0.3 and the cells were washed three times in an equal volume of PBS. An aliquot of the cell suspension was removed to determine cell density. Incorporation of the radioactive label was determined in whole cells in duplicate. Quaternary amine structures were detected using a colorimetric reagent (Dragendorff's reagent) on compounds which were spotted and then dried onto cellulose sheets (EM Science, Cherry Hill, N.J.) (Beiss, 1964, J. Chromatography 13:104).

Transformation of *H. influenzae*

*H. influenzae* was made competent by the method of Herriot et al. (1970, J. Bacteriol. 101:517–524). Preparation of genomic DNA from *H. influenzae* has been described (Hoiseth et al., 1995, Infect. Immun. 49:389–395). Transformants were selected on medium containing tetracycline (1 $\mu$g/ml).

Western Transfer and Immunoblotting

Electrotransfer onto Immobilon-P (Millipore Co, Bedford, Mass.), and Western blotting was carried out as

TABLE 1

Haemophilus Influenzae Strains

| STRAIN | GENOTYPE OR CHARACTERISTICS | TEPC-15 REACTIVITY*+ | SOURCE OR REFERENCE |
|---|---|---|---|
| Eagan | serotype b clinical isolate | +, Pv | Collection of A. Smith |
| Fuju | serotype b clinical isolate | +, Pv | (18)[†] |
| RM7004 | serotype b clinical isolate | +, Pv | (32)[†] |
| RM7004-AH1-2 | lic 1-, tet[r] | — | (21)[†] |
| RM7004-EX1 | lic 2-, tet[r] | — | (21)[†] |
| RM7004-RVdel8 | lic 3-, kan[r] | +, Pv | (17)[†] |
| 169 | Rd⁻, deep rough LPS mutant | — | (35)[†] |
| Rd⁻ | serotype d clinical isolate, unencapsulated | +, Pv | (18) |
| H325 | Rd⁻x RM7004-AH1-2 DNA tet[r] | — | This study |
| H324 | Rd⁻x RM7004-EX1 DNA tet[r] | +, Pv | This study |
| H329 | Eagan x RM7004-AH1-2 DNA tet[r] | — | This study |
| H328 | Eagan x RM7004-EX1 DNA tet[r] | +, Pv | This study |
| H137 | nontypable clinical isolate | +, Pv | This study |
| H143 | nontypable clinical isolate | +, Pv | This study |
| H233 | nontypable clinical isolate | +, Pv | This study |

*Reactivity with MAb TEPC-15 with specificity for phosphorylcholine was determined using Western blotting.
+Reactivity with phase variation (PV) of the TEPC-15 epitope was determined by colony immunoblotting.
(17)[†] Maskell et al., 1991, Mol. Microbiol. 5: 1013–1022.
(18)[†] Weiser, 1993, 3. Infect. Dis. 168: 672–680.
(21)[†] Weiser et al., 1990, Infect. Immun. 58: 3455–3457.
(32)[†] Weiser et al., 1989, Infect. Immun. 57: 3045–3052.
(35)[†] Zamze et al., 1987, Biochem. J. 245: 583–587.

LPS Analysis

*H. influenzae* LPS was prepared from mid-log phase cultures using a hot phenol/water extraction method (Johnson et al., 1976, Can. J. Microbiol. 22:29–34). Cells used in LPS preparation had >97% of the desired phenotype as confirmed by colony immunoblotting. LPS size was assessed in 16.6% acrylamide gels utilizing tricine-sodium dodecyl sulfate polyacrylamide gel electrophoresis (SDS-PAGE) (Lesse, et al., 1990, J. Immunol. Methods described (Towbin et al., 1979, Proc. Natl. Acad. Sci. USA 76:4350–4354). Immunoblotting of membranes was carried out in a 1 in 10,000 dilution of MAb TEPC-15 and bands were visualized following incubation in goat anti-mouse immunoglobulin A antibody conjugated to alkaline phosphatase (Sambrook et al., 1989, supra).

Autoradiography

LPS was prepared from mid-log phase cultures by treatment of whole cell lysates with proteinase K (Boehringer Mannheim, Germany) according to the method of Kimura et al. (1986, supra). LPS was separated on 18% SDS-PAGE gels and was transferred to Immobilon. Immobilon was used for autoradiography following treatment with EN$^3$HANC (Dupont NEN Research Products, Boston, Mass.) according to the manufacturer's instructions.

Colony Immunoblotting

Procedures used for immunoblotting colonies lifted onto nitrocellulose were conducted as described (Weiser et al., 1989, Infect. Immun. 57:3045–3052).

Tissue culture supernatant containing MAb 12D9 was used at a dilution of 1:100 and binding of antibody was detected using goat anti-rabbit immunoglobulin G antibody conjugated to alkaline phosphatase. ChoP was detected on colonies lifted onto nitrocellulose using MAb TEPC-15 as described herein for Western blotting.

Serum Bactericidal Assays

Complement-mediated serum bactericidal activity was determined in normal human serum (NHS) pooled from six random adult donors and stored at −80° C. Assays were performed using 20 μl mid-log phase organisms (OD$_{650}$ 0.3–0.4) diluted to 10$^4$ CFU/ml, 140 μl Hanks balanced salt solution (GIBCO Laboratories, Grand Island, N.Y.), and 20 μl serum. After incubation for 60 minutes at 37° C. with rotation, the reaction was stopped by cooling to 4° C. To calculate the percent survival, colony counts were compared to controls in which complement activity had been eliminated by prior heating of the serum to 56° C. for 30 minutes.

The LPS Core of *H. influenzae* Contains Phosphorylcholine

Figure 2B:

The presence of phosphorylcholine (ChoP) in *H. influenzae* was examined by screening whole cell lysates on Western blots using the MAb TEPC-15, which is specific for ChoP (FIG. 1) (Leon et al., 1971, Biochemistry 10:1424–1429). This MAb cross-reacts with ChoP on the lipoteichoic acid of *S. pneumoniae* forming a ladder-like pattern caused by different numbers of repeating units (Fischer et al., 1993, Eur. J. Biochem. 215:851–857). TEPC-15 was observed to react with low molecular weight material from whole cell lysates of the two unrelated *H. influenzae* strains initially tested, Eagan and Rd⁻. The small molecular weight and interstrain size differences in the TEPC-15 reactive molecule in *H. influenzae* suggested that the MAb was binding to LPS. This was confirmed by Western analysis demonstrating the presence of the TEPC-15 epitope on purified LPS from strains Eagan and Rd⁻, wherein the LPS was obtained using a hot phenol/water extraction method (FIG. 2A). Silver staining of the LPS demonstrated that there was no significant protein contamination (FIG. 2B). This represents the first report of the presence of choline in the LPS of a Gram-negative organism, although in *Escherichia coli*, ethanolamine, which is structurally related to choline, is linked to both KDO and heptose in the LPS inner core region (Raetz, 1996, In: *Escherichia coli* and *Salmonella*, pp. 1035–1063, Neidhardt, Eds., ASM Press, Washington, D.C.).

To determine whether ChoP resides on the lipid or carbohydrate portion of the LPS, strain 169 of *H. influenzae* was analyzed. This deep rough mutant has a truncated LPS consisting of lipid A linked to a single phosphorylated KDO (Zamze et al., 1987, Biochem. J. 245:583–587). The absence of the TEPC-15 antigen in 169 indicates that ChoP resides on the heptose and/or hexose portion of LPS (Table 1) (Zamze et al., 1987, J. Gen. Microbiol. 133:1443–1451; Schweda et al., 1993, Carbohydrate Research 246:319–330). The precise LPS structure(s) to which ChoP is linked has not been determined in this study.

Choline is Obtained From Growth Medium

Figures 3A, 3B, 3C:
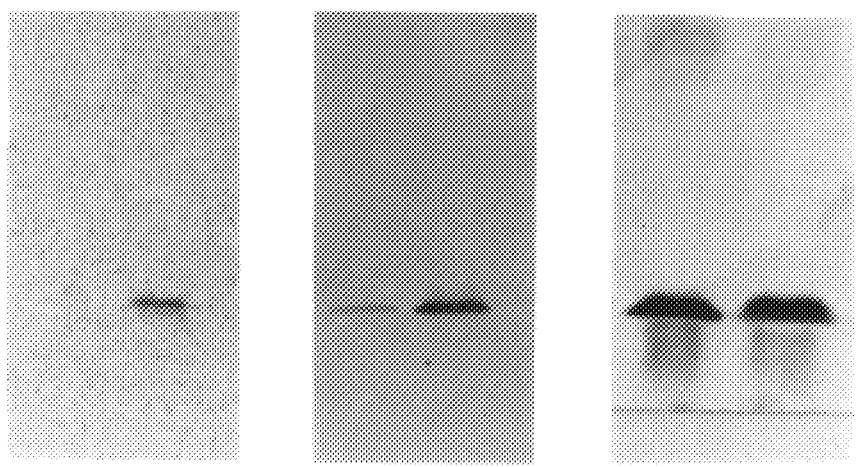
FIG. 3 are photographs of gels depicting autoradiography of TEPC-15-reactive and non-reactive variants grown in the presence of [$^3$H]-choline. LPS in whole-cell lysates was treated with proteinase K, separated in 18% SDS-PAGE gels and detected by autoradiography (FIG. 3A). Controls in which LPS was detected by Western analysis with TEPC-15 (FIG. 3B), or silver staining (FIG. 3C) confirmed the phenotype and the equivalency of the loading samples. Lanes 1: Rd⁻ (TEPC-15 non-reactive variant); Lane 2: Rd⁻ (TEPC-15 reactive variant). Size markers are protein standards in kilodaltons.

Choline is not essential for growth of *H. influenzae* since a chemically defined growth medium lacking choline has been described for this organism (Michalka, 1969, J. Mol. Biol. 45:407–421). However, similar to *S. pneumococcus*, *H. influenzae* acquires choline from the growth medium. This was established as follows. [$^3$H]-Choline was added to supplemented brain-heart infusion medium which also contained an unspecified quantity of unlabeled choline. The incorporation of [$^3$H]-choline from the medium into LPS was demonstrated by autoradiography. The radioactivity co-migrated with the LPS bands which were reactive with TEPC-15 and were detected by silver staining in whole-cell lysates treated with proteinase K and separated by SDS-PAGE (FIG. 3). The incorporation of [$^3$H]-choline into LPS confirms the fact that this *H. influenzae* glycolipid contains choline. Based on reactivity with TEPC-15, which has high affinity for ChoP but not for choline, the substituent on the LPS is in the form of choline phosphate (ChoP) (Leon et al., 1971, supra).

Incorporation of Choline Undergoes Phase Variation

In addition to serotypes b (Eagan) and d (Rd⁻) strains, a number of other *H. influenzae* strains were screened for the presence of ChoP on LPS. All strains examined, including two additional serotype b isolates (RM7004 and Fuju) and three unrelated nontypable isolates (H137, H143 and H233), exhibited the TEPC-15 epitope on their surface as assessed by Western analysis (Table 1). It was concluded that the presence of ChoP is a common and possibly ubiquitous feature of *H. influenzae*.

Figure 4A:
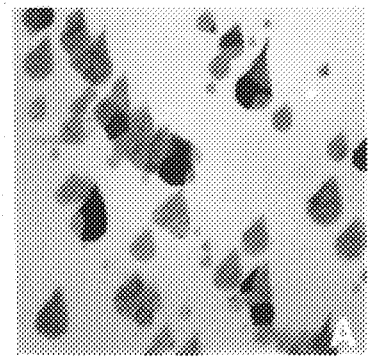
FIG. 4A is an immunoblot of colonies of strain RM7004 showing sectoring, using MAb TEPC-15.

In examining the above-described *H. influenzae* strains, considerable strain to strain variation was noted in the intensity of reactivity of the organisms to TEPC-15. Since the LPS of this organism displays marked phase variation in structure, intrastrain difference in content of ChoP was assessed using TEPC-15 on colony immunoblots. Each of the seven strains shown to have ChoP-LPS displayed colony to colony variation in expression of the TEPC-15 epitope (Table 1). The observation of sectored colonies and reversion of reactive to non-reactive colonies as well as non-reactive to reactive colonies indicated that intrastrain differences were the result of phase variation of the TEPC-15 antigen (FIG. 4A).

Phase variation in the TEPC-15 epitope allowed for the separation of organisms into two relatively uniform populations based on reactivity with the MAb. Purified LPS from reactive and non-reactive phase variants of strains Eagan and Rd⁻ were compared following separation on tricine SDS-PAGE gels. Variation in expression of the TEPC-15 epitope in colonies correlated with variation in expression of the TEPC-15 reactive structure in LPS assessed by Western analysis (FIG. 2A). Silver staining of LPS from reactive and non-reactive phase variants demonstrated equivalent loading and established that there were slight differences in LPS migration between variants. However, the relationship between the presence of the TEPC-15 epitope and LPS size was not consistent among the two strains (FIG. 2B).

Figure 5:
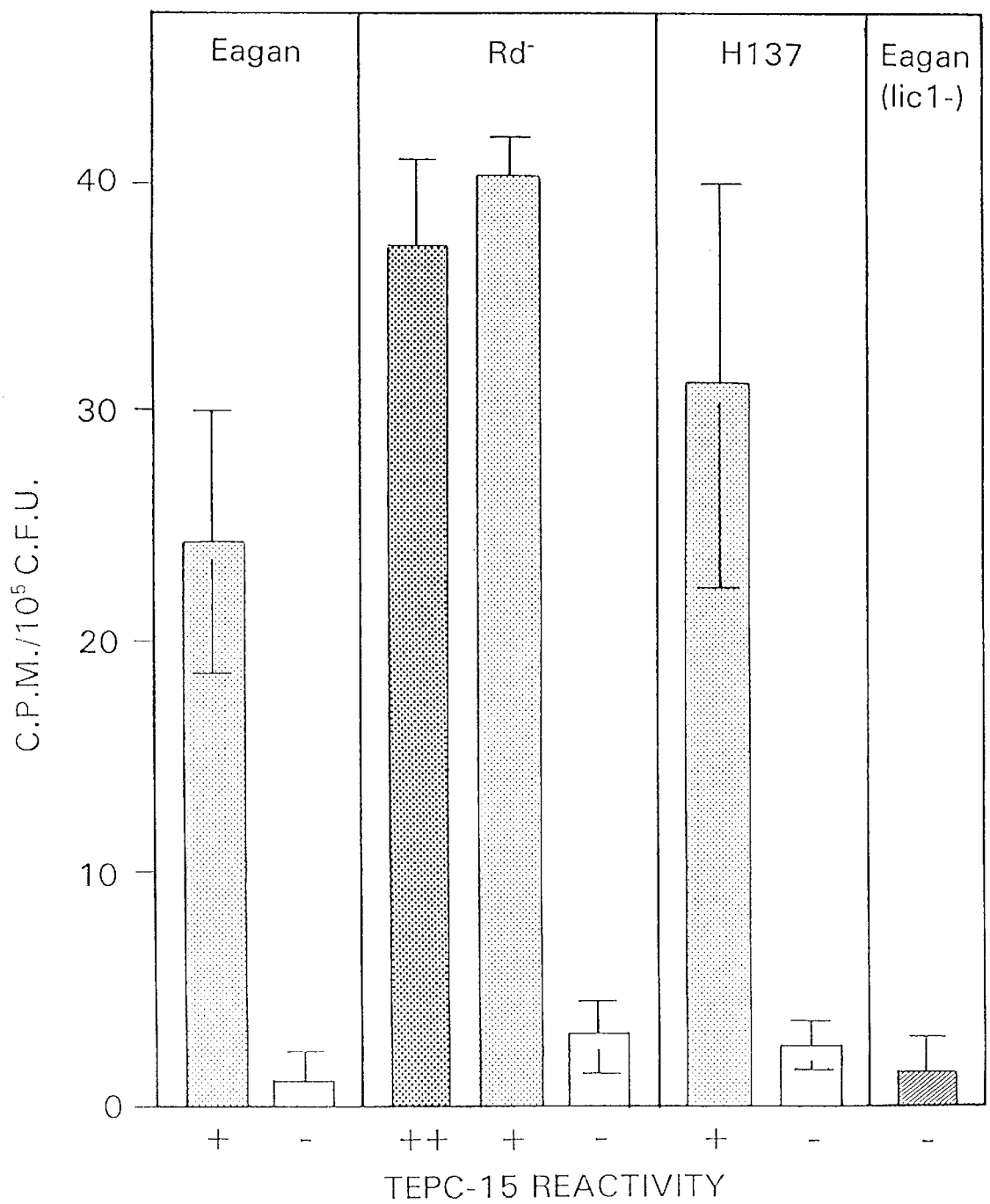
FIG. 5 is a graph depicting a comparison of the incorporation of [$^3$H]-choline in phase variants that differ in reactivity with MAb TEPC-15. A single colony that was either reactive (stippled or solid bars) or non-reactive (open bars) with TEPC-15 on colony immunoblots was grown in the presence of radiolabeled choline to mid-log phase. Incorporation of [$^3$H]-choline into whole cells was determined and expressed as the number of counts per minute (cpm) in $10^5$ colony forming units (cfu)±standard deviation. For strain Rd⁻, variants having three levels of reactivity to TEPC-15 were compared. [$^3$H]-choline incorporation in strain H329, a lic1-mutant of strain Eagan, is shown as a hatched bar.

In addition, [$^3$H]-choline incorporation into whole cells was assessed for TEPC-15 reactive and non-reactive variants of three unrelated strains (Rd⁻, Eagan and H137). In each case, those variants having ChoP were able to incorporate [³H]-choline (FIG. 5). In contrast, variants lacking the TEPC-15 epitope incorporated approximately 15–30 fold less of the radiolabeled choline. This result demonstrates that the ability to incorporate choline acquired from the nutrient medium correlates with expression of ChoP on LPS.

The separation of variants also allowed for a simple colorimetric assay to confirm the presence of choline on LPS. Dragondorff's reagent reacts with quaternary amines such as choline, but not with non-quaternary amines that are structural analogs of choline, such as ethanolamine (Beiss, 1964, supra). Dragondorff's reagent was observed to react with purified LPS from TEPC-15 reactive variants of strains Eagan and Rd⁻, but not with an equal quantity of purified LPS from TEPC-15 non-reactive variants of these strains (FIG. 2). In control experiments, the reagent reacted with choline and ChoP, but not with ethanolamine or phosphorylethanolamine. These results provide physical evidence that *H. influenzae* LPS undergoes phase variation in expression of a quaternary amine structure, which based on incorporation of choline and reactivity with the MAb TEPC, is ChoP.

lic1 is Necessary for Choline Incorporation

The relationship between phase variation in ChoP and phase variation in LPS structures determined by the three lic loci was examined in strain RM7004 from which these loci were initially characterized. Mutants with deletion/insertion mutations encompassing all open reading frames in each locus were compared to the parent strain for reactivity with TEPC-15 on colony immunoblots (Table 1). Mutants in lic1 (RM7004-AH1-2) and lic2 (RM7004-EX1) were constitutively non-reactive, whereas a mutation in lic3 (RM7004-RVdel8) had no effect on this epitope.

In order to confirm the role of these loci in the expression of ChoP, chromosomal DNA from the lic1 and lic2 mutants in RM7004 was transferred into strains Eagan and Rd⁻. In the case of both strain Eagan and Rd⁻, acquisition of tetracycline resistance from the lic1 mutant, but not the lic2 mutant, correlated with constitutive loss of reactivity with TEPC-15 (Table 1).

Additional evidence that lic1 is necessary for decorating the LPS with ChoP was provided in experiments using colony immunoblots. The pattern of variation in reactivity with TEPC-15 correlated precisely with the expression of the LPS epitopes defined by MAb 12D9 and expressed by lic1 (FIG. 4; B and C). There was no correlation between expression of the 4C4 epitope encoded by lic2 and reactivity with TEPC-15. Further, a defined mutant in lic1 (H329), was unable to incorporate large amounts of [³H]-choline from the medium (FIG. 5). These results suggest that the lic1 locus is necessary for incorporation of choline, whereas LPS structures expressed by the lic2 locus may be required only in some strains.

The Contribution of lic1 Genes to Choline Incorporation

The data described below provide evidence that lic1 functions directly in the incorporation of ChoP onto the LPS. The four gene products of the lic1 locus were compared to other sequences available in sequence databases. For this comparison, the BLAST program was used through the National Center for Biotechnology Information (Altschul et al., 1990, J. Mol. Biol. 215:403–410).

The first gene in lic1, licA, encodes a polypeptide having sequence similarity to choline kinases in *Saccharomyces cerevisiae* (30.8% identity and 54.4% similarity over 68 amino acids), *Caenorhabditis elegans* (50.0% identity and 63.9% similarity over 36 amino acids), and in rat liver (FIG. 7) (Uchida et al., 1992, J. Biol. Chem. 267:10156–10162). The region of greatest similarity is within the consensus sequence, HXDhXXXNhhh [SEQ ID NO: 17] (where h is a large hydrophobic peptide, FLIMVMY), which contains the catalytic domain for phosphotransferases and protein kinases reported by Brenner (Brenner, 1987, supra). The similarity to other choline kinases, including the active site of the enzyme in a protein whose function is linked to choline incorporation, indicates that LicA may function as a bacterial choline kinase.

The second gene in lic1, licB, encodes a protein comprised of nine hydrophobic domains. This protein exhibited sequence similarity with several proteins including a membrane protein from *Clostridium kluyveri* (26.2% identity and 41.8% similarity over 194 amino acids). Although the function of this protein is unknown, it is notable that some species of the genus Clostridium have been found to have ChoP containing cell walls (Povdin et al., 1988, J. Gen. Microbiol. 134:1603–1609). There is also similarity between LicB and the chloroplast triose phosphate transporter in plants (24% identity and 47% similarity over 183 amino acids for the triose phosphate transporter of *Spinacia oleracea*). The triose phosphate transporter is an anion selective channel protein in the chloroplast envelope which transports fixed carbon as triose phosphate into the cytoplasm (Flugge et al., 1991, Nature 353:364–367; Schwartz et al., 1994, J. Biol. Chem. 269:29481–29489). A separate region of LicB resembles the high-affinity choline permease, BetT (41.2% identity and 66.7% similarity over 51 amino acids), identified in strain Rd⁻ by its similarity to the *E. coli* gene (Lamark et al., 1991, Mol. Microbiol. 5:1049–1064; Fleischmann et al., 1995, Science 269:497–512).

The third gene in lic1, licC, encodes a protein having an N-terminus which resembles the allosteric site of a family of pyrophosphorylases that catalyze reactions between nucleoside triphosphates and sugar 1-phosphates during the biosynthesis of polysaccharide. Of five groups of pyrophosphorylases, LicC is most similar to uridylyltransferases such as α-glucose-1-phosphate uridylyltransferase which is involved in spore coat polysaccharide biosynthesis in *Bacillus subtilis* (42% identical and 63% similar over 52 amino acids) (Glaser et al., 1993, Mol. Microbiol. 10:371–384).

The last gene in lic1, licD, encodes a protein having similarity to a gene cpsG, that has been identified in *S. pneumoniae* within the locus for synthesis of the capsular polysaccharide (38% identity and 64% similarity over 65 amino acids) (Guidolin et al., 1994, Infect. Immun. 62:5384–5396).

Figure 7:
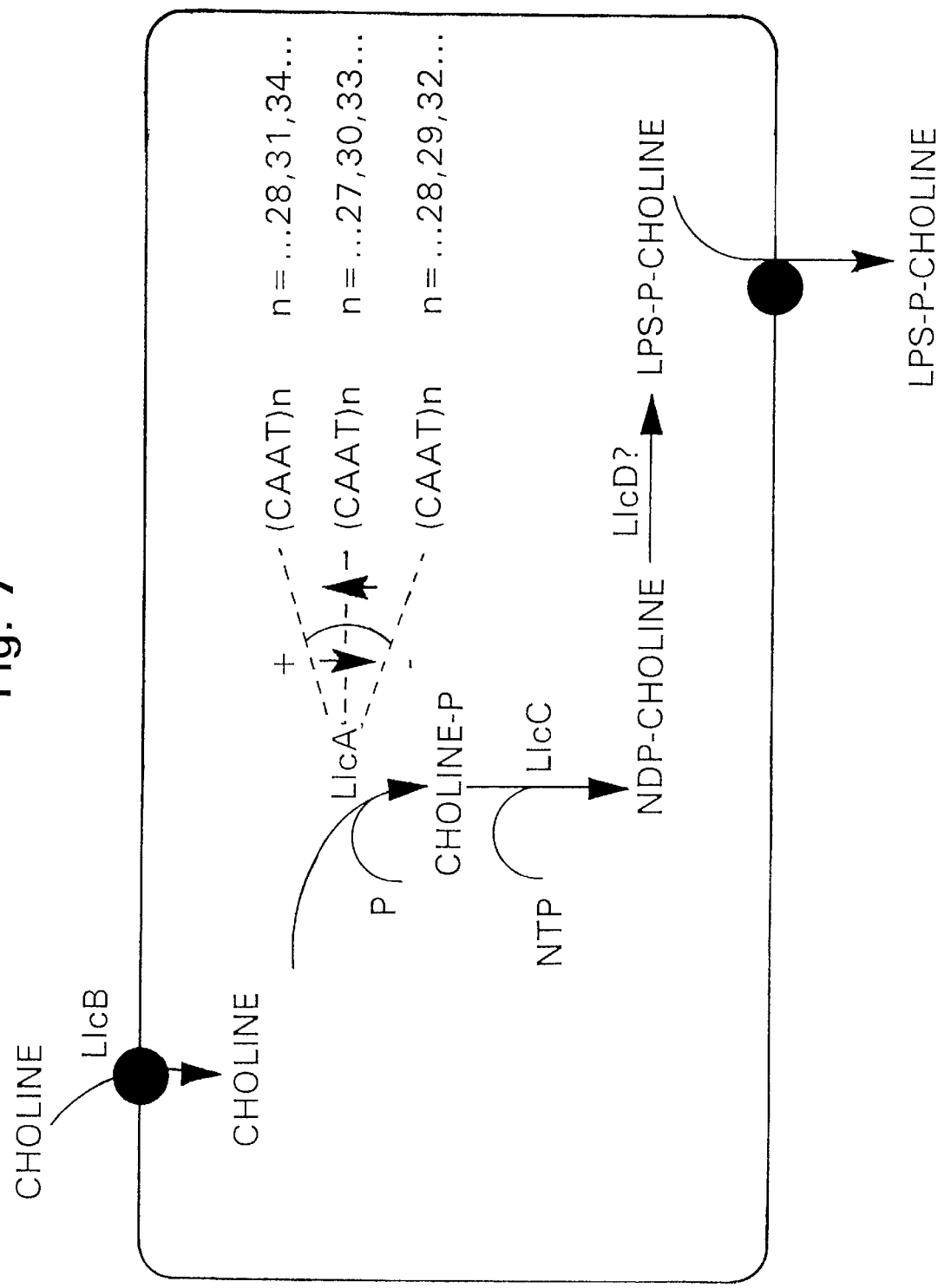
FIG. 7 is a diagram of a possible pathway for choline incorporation in *H. influenzae.* The role of LicA-D in the uptake and incorporation of choline as phosphorylcholine on the LPS is proposed based on sequence similarity to other enzymes. Translation of licA into a full-length protein requires the correct number (n) of intragenic CAAT repeat units, which is variable as shown.

The mechanism by which choline is incorporated into LPS in *H. influenzae* has features in common with the mechanism of choline incorporation into eukaryotic lipids. The most likely mechanism of choline incorporation into *H. influenzae* is shown in FIG. 7 and is summarized below. Following phosphorylation by choline kinase (LicA), a pyrophosphorylase (LicC) likely catalyzes the formation of nucleoside diphosphocholine from choline phosphate and a nucleoside triphosphate (perhaps UTP). There is evidence that LicB is a membrane associated transporter of small organophosphate molecules and that it interacts with choline. LicB may thus be involved in transport of choline across the membrane. The proposed mechanism predicts that the final step in the pathway is transfer of the activated form of choline onto the LPS. While there is no specific evidence suggesting LicD transfers ChoP onto the LPS, similarity to a gene which functions in polysaccharide synthesis provides a link between other lic genes that appear to interact with choline and the oligosaccharide of *H. influenzae*.

Figure 4D:
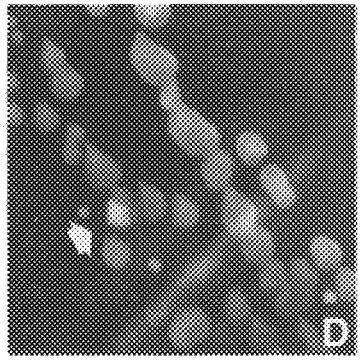
FIG. 4D is a photograph of a variant colony of strain Eagan with the opaque phenotype, (white arrow).
Figure 4B:
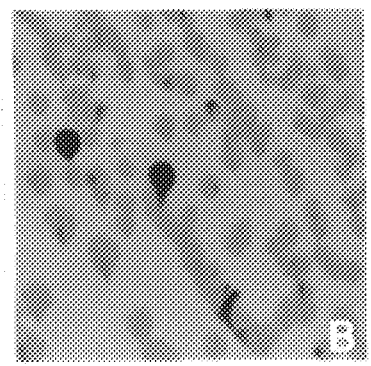
FIG. 4B is an immunoblot of colonies of strain Eagan immunoblotted with MAb TEPC-15.
Figure 4E:
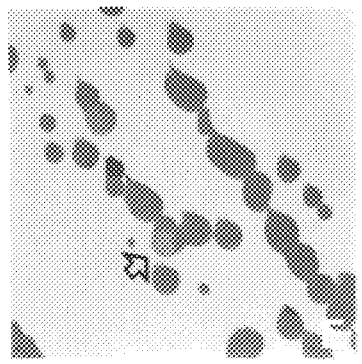
FIG. 4E depicts the same colony as in FIG. 4D exhibiting diminished reactivity when immunoblotted with TEPC-15 (open arrow).
Figure 4C:
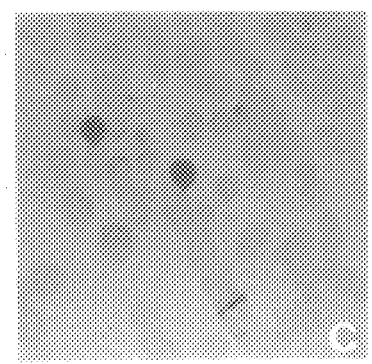
FIG. 4C is a photograph of the same colonies shown in FIG. 4B which were regrown and immunoblotted with MAb 12D9, whose epitope undergoes phase variation controlled by the lic1 locus.
Figure 4F:
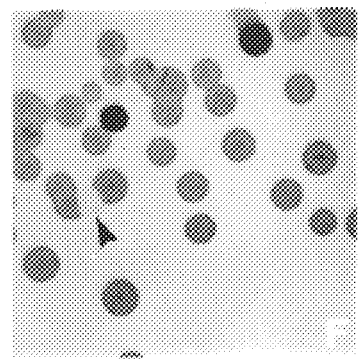
FIG. 4F is an immunoblot of strain H233 exhibiting three distinct levels of reactivity with TEPC-15; high reactivity, low reactivity and non-reactive (indicated by an arrow).

Relationship Between Phase Variation in Phosphorylcholine and Other LPS Structures Three distinct levels of reactivity with TEPC-15 (negative, low and high) among each of the strains which were analyzed were noted in experiments using colony immunoblots. This suggests that phase variation of ChoP may be more complicated than on-off switching (FIG. 4F). Similar observations were made with the lic1 associated epitope defined by MAb 12D9. It was observed that two of the three reading frames of licA have possible initiation codons, which if translated into a full-length polypeptides, could led to two forms of LicA differing at the N-terminus. The three observed phenotypes could result from variation between the three reading frames of licA. Alternatively, phase variation between three phenotypes may be reflected in the fact that binding of TEPC-15 to ChoP on the LPS is affected by the presence or absence of other variably expressed LPS structures, rather than differences in the amount of incorporated choline. Results of experiments demonstrating no difference in incorporation of radiolabeled choline from phase variants of strain Rd$^-$ having high and low levels of reactivity with TEPC-15 support this possibility (FIG. 5).

Another factor in the expression of the TEPC-15 epitope is colony opacity. Although both opaque and transparent phenotypes were capable of expressing the TEPC-15 epitope, the opaque colony morphology exhibited diminished reactivity with TEPC-15 compared with variants having a transparent phenotype (FIGS. 4D and E). This indicates that undefined LPS structures associated with opaque organisms may affect the ability of TEPC-15 to bind to its epitope on the LPS.

Contribution of Phosphorylcholine to Serum Sensitivity

Figure 8:
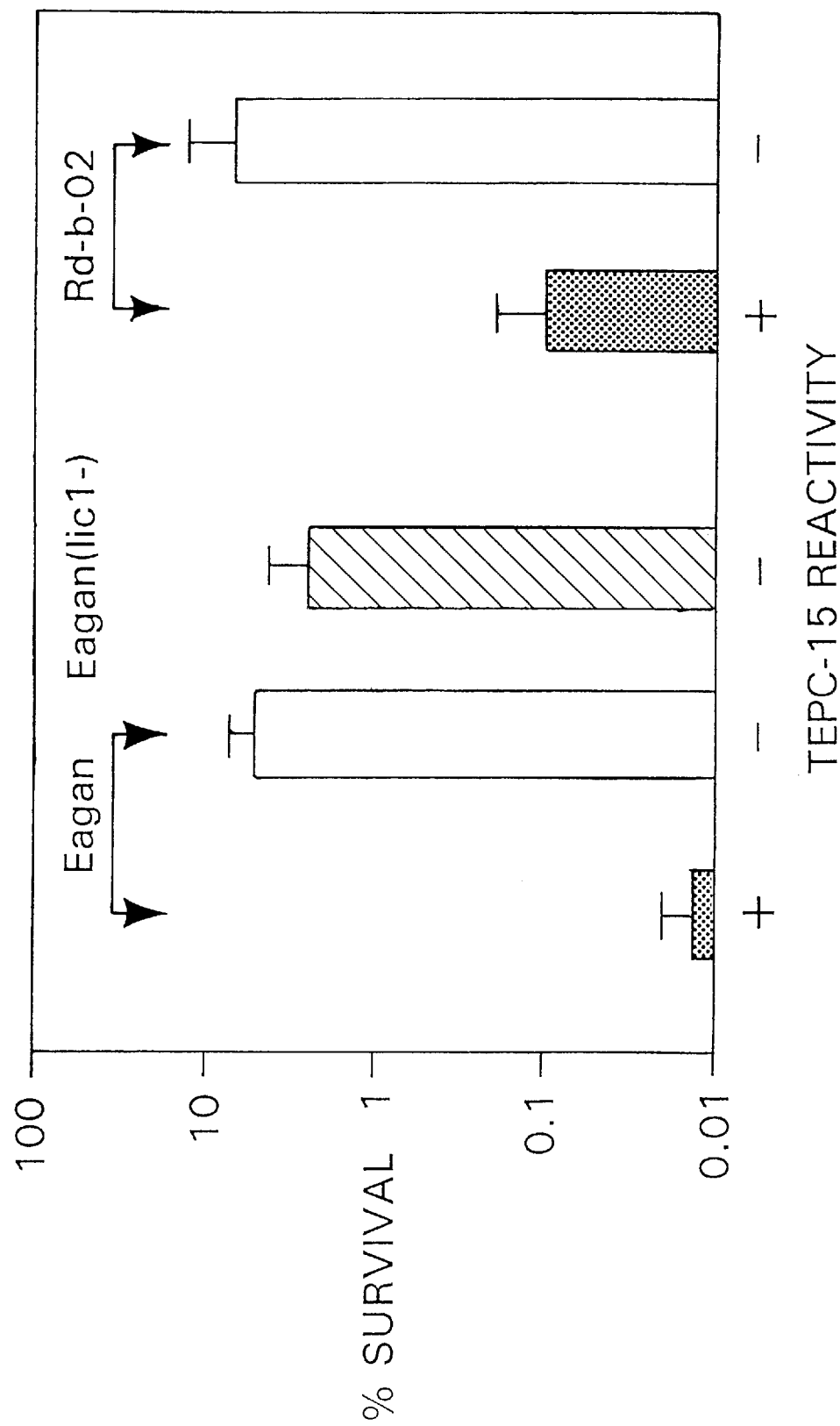
FIG. 8 is a graph depicting a comparison of the resistance of *H. influenzae* phase variants to the bactericidal activity of human serum. A single TEPC-15 reactive (stippled bar) or non-reactive (open bar) colony of strain Eagan or its lic1-mutant (hatched bar), H329, were grown to mid-log phase and treated for 60 minutes in 10% pooled normal human serum. The percentage survival is the number of colony forming units remaining compared to controls in which complement was inactivated±standard deviation.

The possibility that expression of ChoP on the cell surface contributes to antigenic variation was examined. The effect of ChoP on the ability of *H. influenzae* to evade the bactericidal action of complement and antibody in human serum was assessed using the encapsulated strain Eagan having a transparent colony phenotype. Phase variants having ChoP were more than two-hundred-fold more sensitive to serum than were phase variants which do not have ChoP on LPS (FIG. 8). ChoP-containing variants were also significantly more serum sensitive than a constitutive ChoP negative mutant of strain Eagan in which the lic1 locus had been interrupted. Expression of ChoP on the LPS by lic1 therefore renders the organism more rather than less serum sensitive.

However, since other respiratory tract pathogens also contain ChoP on the cell surface (Ladefoged et al., 1994, J. Bacteriol. 176:5835–5842), the occurrence of ChoP on the *H. influenzae* cell surface is predicted to contribute to the ability of this pathogen to thrive in the human respiratory tract.

The data described herein thus establish that lic gene products facilitate the addition of choline onto cell surface components of bacteria. This discovery has provided a means of identifying compounds having antibiotic activity, which compounds may be useful as antibiotics directed against *H. influenzae* and other bacteria.

Isolation of S. pneumoniae Choline Kinase Gene

A homolog of *H. influenzae* choline kinase has also been discovered in *S. pneumoniae*. This discovery was made using degenerate oligonucleotides based on the active site of choline kinase and PCR. The primers used were: Forward 5'TGYCAYATYGAYTTRGTNCCWGARAAY3' [SEQ ID NO: 18] Reverse 5'RTARTCRCCRAARTTYTCWCCNT-GYTCYTCYTT3' [SEQ ID NO 19] where R is G/A, Y is C/T, W is A/T, M is A/C, K is G/T, S is C/G, H is A/C/T, V is A/C/G, B is C/G/T, D is A/G/T and N is A/G/T/C.

A *S. pneumoniae* DNA fragment was obtained, sequenced and the deduced amino acid sequence was also obtained (FIG. 9). The deduced amino acid sequence of *S. pneumoniae* choline kinase was compared to that of *H. influenzae* and to that of *Mycoplasma pneumoniae* (FIG. 10).

In addition, using the BLAST program, the similarity of various regions of the *S. pneumoniae* choline kinase was compared with that of *H. influenzae* (FIG. 11).

DNA was extracted from *S. pneumoniae* and was hybridized to the PCR amplified *S. pneumoniae* choline kinase fragment obtained as described above. The results establish that this fragment resides on the genome of *S. pneumoniae*.

The invention should not be construed to be limited solely to *H. influenzae* and *S. pneumoniae* choline kinase genes. Using the procedures described herein, it has also been possible to identify choline on the cell surface of *Neisseria gonorrhea*, *Neisseria meningiditis* and in *Pseudomonas aeruginosa*. Using the procedures described herein, it is now possible to isolate choline kinase genes from these organisms for use in methods of identifying compounds capable of inhibiting the growth of these organisms.

The disclosures of all patents, patent applications, and publications cited herein are hereby incorporated herein by reference in their entirety.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A method of identifying a compound capable of disrupting the addition of choline onto a bacterial cell surface component comprising incubating a sample of bacteria in a solution containing choline in the presence or absence of a test compound, and assessing the effect of said test compound on the addition of choline onto said bacterial cell surface component, wherein a lower level of choline on said cell surface component in the presence of said test compound, compared with the level of choline on said cell surface component in the absence of said test compound, is an indication that said test compound inhibits the addition of choline onto said cell surface component.

2. The method of claim 1, wherein said cell surface component is a cell wall component.

3. The method of claim 2, wherein said cell surface component is selected from the group consisting of lipopolysaccharide, teichoic acid, lipoteichoic acid, protein and glycoprotein.

4. The method if claim 1, wherein said bacteria are selected from the group consisting of *H. influenzae* and *S. pneumoniae*.

5. A method of identifying a compound capable of disrupting the addition of choline onto a bacterial cell surface component comprising incubating a bacterial extract in a solution containing choline in the presence or absence of a test compound, and assessing the effect of said test compound on the addition of choline onto said bacterial cell surface component, wherein a lower level of choline on said cell surface component in the presence of said test compound, compared with the level of choline on said cell surface component in the absence of said test compound, is an indication that said test compound inhibits the addition of choline onto said cell surface component.

6. The method of claim 5, wherein said cell surface component is a cell wall component.

7. The method of claim 6, wherein said cell surface component is selected from the group consisting of lipopolysaccharide, teichoic acid, lipoteichoic acid, protein and glycoprotein.

8. The method if claim 5, wherein said bacterial extract is obtained from bacteria selected from the group consisting of *H. influenzae* and *S. pneumoniae*.

9. A method of identifying a compound capable of disrupting the addition of choline onto a bacterial cell surface component comprising incubating an isolated preparation of a bacterial choline kinase in a solution containing choline in the presence or absence of a test compound, and assessing the effect of said test compound on the addition of choline onto said bacterial cell surface component, wherein a lower level of choline on said cell surface component in the presence of said test compound, compared with the level of choline on said cell surface component in the absence of said test compound, is an indication that said test compound inhibits the addition of choline onto said cell surface component.

10. The method of claim 9, wherein said cell surface component is a cell wall component.

11. The method of claim 10, wherein said cell surface component is selected from the group consisting of lipopolysaccharide, teichoic acid, lipoteichoic acid, protein and glycoprotein.

12. The method if claim 9, wherein said bacterial choline kinase is elected from the group consisting of *H. influenzae* and *S. pneumoniae* choline kinase.

13. A compound capable of disrupting the addition of choline onto a bacterial cell surface component identified by the method of claim 1.

14. A compound capable of disrupting the addition of choline onto a bacterial cell surface component identified by the method of claim 5.

15. A compound capable of disrupting the addition of choline onto a bacterial cell surface component identified by the method of claim 9.

* * * * *